United States Patent
De Laporte et al.

(10) Patent No.: US 11,071,806 B2
(45) Date of Patent: Jul. 27, 2021

(54) MACROSCOPICALLY ALIGNABLE, INJECTABLE, SOFT HYDROGEL COMPOSITION

(71) Applicant: DWI-LEIBNIZ-INSTITUT FÜR INTERAKTIVE MATERIALIEN E.V., Aachen (DE)

(72) Inventors: Laura De Laporte, Meerbusch (DE); Martin Möller, Aachen (DE); Jonas Christopher Rose, Düsseldorf (DE); Abdolrahman Omidinia-Anarkoli, Aachen (DE)

(73) Assignee: DWI—LEIBNIZ-INSTITUT FÜR INTERAKTIVE MATERIALIEN E.V., Aachen (DE)

( * ) Notice: Subject to any disclaimer, the term of this patent is extended or adjusted under 35 U.S.C. 154(b) by 0 days.

(21) Appl. No.: 16/331,454

(22) PCT Filed: Sep. 25, 2017

(86) PCT No.: PCT/EP2017/001142
§ 371 (c)(1),
(2) Date: Mar. 7, 2019

(87) PCT Pub. No.: WO2018/054542
PCT Pub. Date: Mar. 29, 2018

(65) Prior Publication Data
US 2019/0216979 A1 Jul. 18, 2019

(30) Foreign Application Priority Data
Sep. 26, 2016 (EP) .................................... 16002078

(51) Int. Cl.
*A61L 27/44* (2006.01)
*A61L 27/48* (2006.01)
*A61L 27/52* (2006.01)
*A61L 27/04* (2006.01)

(52) U.S. Cl.
CPC .......... *A61L 27/446* (2013.01); *A61L 27/042* (2013.01); *A61L 27/48* (2013.01); *A61L 27/52* (2013.01); *A61L 2400/06* (2013.01)

(58) Field of Classification Search
CPC .......... A61L 27/44; A61L 27/48; A61L 27/52; A61L 27/04
See application file for complete search history.

(56) References Cited

U.S. PATENT DOCUMENTS

2016/0374950 A1* 12/2016 Yacoub .................. A61K 33/00
424/493

FOREIGN PATENT DOCUMENTS

WO 2014/021954 A2 2/2014

OTHER PUBLICATIONS

Ji et al. Polymers (2012) 4,316-340.*
Ivaneyko et al. (Soft Matter, (2015), 11,7627).*
These de Monsieur Pol-Edern Le Renard (Jun. 19, 2012).*
Lagerwall et al. Current Applied Physics 12(2012) 1387-1412).*
Chau et al. Chemistry material (2016); 28, 3406-3415).*
International Search Report dated Apr. 16, 2018, for corresponding International Patent Application No. PCT/EP2017/001142.
Written Opinion dated Apr. 16, 2018, for corresponding International Patent Application No. PCT/EP2017/001142.
International Preliminary Report on Patentability dated Sep. 14, 2018, for corresponding International Patent Application No. PCT/EP2017/001142.
Zhang, et al., A self-assembly pathway to aligned monodomain gels, Nat. Mater, 2010, 9(7), 594-601.
Berns, et al., Aligned neurite outgrowth and directed cell migration in self-assembled monodomain gels, Biomaterials, 2014, 35(1), 185-195.
Kim, et al., Independent Control of Topography for 3D Patterning of the ECM Microenvironment, Adv. Mater., 2016, 28, 132-137.
Antman-Passig, et al., Remote magnetic orientation of 3D collagen hydrogels for directed neuronal regeneration, Nano Lett., 2016, 16(4), 2567-2573.
Fergal J. O'Brien, Biomaterials & scaffolds for tissue engineering, Mar. 1, 2011, XP055354226.
Gupta, et al., Synthesis and surface engineering of iron oxide nanoparticles for biomedical applications, Biomaterials, Elsevier Science Publishers BV., Barking, GB, Jun. 1, 2005, vol. 26, No. 18, 3996-4021.
Sivakumaran, et al., Injectable Microgel-Hydrogel Composites for Prolonged Small-Molecule Drug Delivery, Biomacromolecules, Nov. 14, 2011, vol. 12, No. 11, 4112-4120.
Huang, et al., New fibrin gel prepared by adding template molecules e.g. bovine serum albumin into a fibrinogen gel, and cross-linking and solidifying by thrombin, useful for identifying proteins, WPI/Thompson, Jul. 16, 2008, vol. 2008, No. 68.
T.R. Pisanic, et al., "Nanotoxicity of iron oxide nanoparticle internalization in growing neurons", Biomaterials 28 (2007)2572-2581.
You-Jin Kim, et al., "Translational and rotational motion control of microgels enabling shoaling and schooling", Soft Matter, vol. 11, No. 5, 2015.
J.J. Rice, et al., "Engineering the Regenerative Microenvironment with Biomaterials", Adv. Healthcare Materials, 2(1): 57-71 (2013)).
Fergal J. O'Brien, "Biomaterials & scaffolds for tissue engineering", materialstoday, Mar. 2011, vol. 14, No. 3.

* cited by examiner

*Primary Examiner* — Shirley V Gembeh
(74) *Attorney, Agent, or Firm* — Pergament & Cepeda LLP; Milagros A. Cepeda; Edward D. Pergament

(57) ABSTRACT

The present invention relates to a macroscopically alignable, injectable, soft hydrogel composition which is able to form an anisotropic structure in vivo, after injection, to generate healthy functioning tissue and regenerate injured or diseased soft tissue.

13 Claims, 19 Drawing Sheets

MACROSCOPICALLY ALIGNABLE, INJECTABLE, SOFT HYDROGEL COMPOSITION

Figure 1:
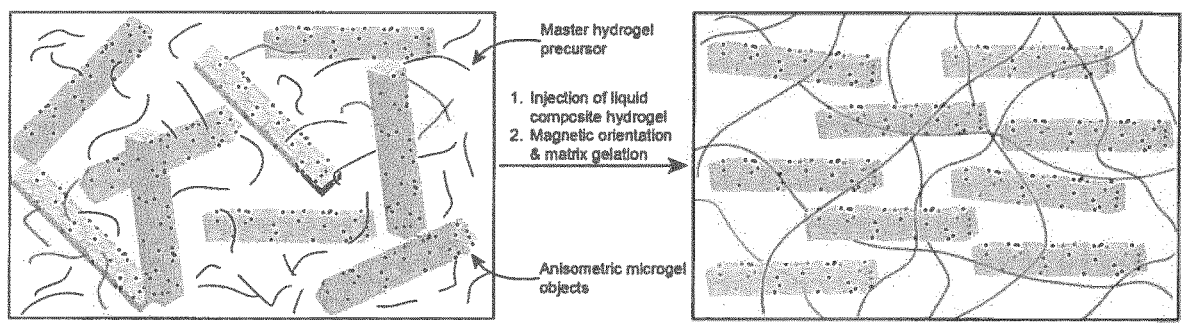

This application is a National Stage Application under 35 U.S.C. § 371 of PCT International Application No. PCT/EP2017/001142, filed Sep. 25, 2017, which takes priority from European Provisional Application Number EP 16002078.0, filed Sep. 26, 2016; all of which is herein incorporated in its entirety.

The present invention relates to a macroscopically alignable, injectable, soft hydrogel composition which is able to form an anisotropic structure in vivo, after injection, to generate healthy functioning tissue and regenerate injured or diseased soft tissue.

Soft tissues have a wide range of mechanical properties, ranging from 200 Pa (spinal cord) to 50 MPa (skin) (C. T. McKee, J. A. Last, P. Russell, C. J. Murphy, Indentation versus tensile measurements of Young's modulus for soft biological tissues. *Tissue Engineering, Part B.* 17, 155-164 (2011)). Implants from hard materials may get covered with scar tissue, whereas an overly soft material can be deformed or degraded mechanically (I. R. Minev et al., Electronic dura mater for long-term multimodal neural interfaces, *Science* 6218, 159-63 (2015)).

In contrast to a preformed implant that can support and substitute large structures such as a partial or whole organ, or large hollow structures (e.g., trachea, large blood vessels) a hydrogel product formulation like those addressed herein can be directed to guide cell organization and by this to improve the healing process. For the envisaged application it must match the mechanical properties of soft and super soft tissue, enable cell ingrowth, migration and proliferation, direct cells into specific directions and enable diffusion of nutrient and cell signaling molecules throughout the matrix.

In some applications, such as spinal cord or heart regeneration, there is no available space for implantation, and removal of part of the tissue could generate more damage. Here, these problems can be avoided by injecting a fluidic product in a minimal invasive manner. The advantage of this minimally invasive surgical procedure is that the product can easily adapt to irregular shapes of a defect, and create an integrative product-tissue interface. Furthermore, injectable matrices are especially suitable in regard to acute (trauma-induced) injuries as remaining functional tissue can still be present and should not be further impaired. Moreover, injectable materials can prevent open surgical implantation procedures.

So far, however, injectable hydrogels lack the anisotropic and hierarchical structure with directionally organized functions and mechanical properties, regenerative matrices have to provide to guide cell organization during the healing process. Therefore, it is a challenge to engineer injectable alignable hydrogels that combine the required compliance and biomolecular functionalization with orientational order.

In general concepts for the formation of anisotropic hydrogels with anisotropic structural properties that can be oriented uniaxially are very limited so far. One example of a hydrogel with anisotropic properties is a peptide hydrogel with monodomain regions of oriented fiber bundles that was introduced by S. Zhang et al. (A self-assembly pathway to aligned monodomain gels, *Nat Mater* 9, 594-601 (2010)). Monodomains of several hundred micrometer size could be formed by mechanical orientation and led to the ability to align neurite outgrowth of dorsal root ganglia (DRGs) in vitro (Aligned neurite outgrowth and directed cell migration in self-assembled monodomain gels, *Biomaterials* 35, 185-195 (2014)). In another approach, spherical magnetic iron oxide particles have been aligned by a magnetic field to form strings within Matrigel®, a reconstituted laminin rich extracellular matrix (ECM) (J. Kim, J. R. Staunton, K. Tanner, Independent Control of Topography for 3D Patterning of the ECM Microenvironment. *Adv. Mater.* 28, 132-137 (2015); M. Antman-Passig, O. Shefi, Remote magnetic orientation of 3D collagen hydrogels for directed neuronal regeneration, *Nano Lett.*, (2016)). These magnetic particles have been coated with different ECM proteins to support cell attachment and their alignment resulted in orientated single fibroblasts and PC12 neuron-like cells. However, cell orientation was observed both parallel and perpendicular to the direction of the particle strings (J. Kim, J. R. Staunton, K. Tanner, Independent Control of Topography for 3D Patterning of the ECM Microenvironment. *Adv. Mater.* 28, 132-137 (2015)). In addition, the movement of magnetic particles was proposed to induce orientation of collagen fibers within a collagen hydrogel, resulting in neurite extension along the particle and fiber orientation (M. Antman-Passig, O. Shefi, Remote magnetic orientation of 3D collagen hydrogels for directed neuronal regeneration, *Nano Lett.*, 16, 2567-2573 (2016)). However, in both cases, the chain-like oriented strings consisted entirely out of iron oxide and their dimensions were determined by the size and amount of the magnetic particles. As the magnetic iron oxide particles decrease viability of sensitive cells and reduce the ability to form neurites of PC12 cells (T. R. Pisanic, J. D. Blackwell, V. I. Shubayev, R. R. Finones, S. Jin, Nanotoxicity of iron oxide nanoparticle internalization in growing neurons, *Biomaterials* 28, 2572-81 (2007)), high iron containing particle amounts may not be applicable for tissue regeneration, involving these cells.

You-Jin Kim et al., Soft Matter, Vol. 11, No. 5, pages 994-1000) discloses spherical microgels containing superparamagnetic iron oxide nanoparticles (SPIONs) where the SPIONs are immobilized by subsequent chemical crosslinking of the microgel. WO 2014/021954 discloses a composition comprising silk-fibroin based material embedded with a plurality of magnetic particles.

Against this background, the technical problem underlying the present invention is to provide an injectable biomaterial, which is able to form an anisotropic structure in vivo, after injection, so that it can be used as a therapeutic material. The structure needs to enable transport of nutrients and cell signaling molecules throughout the material.

These objects are solved by the embodiments defined in the claims.

In particular, the present invention relates to a macroscopically alignable, injectable, soft hydrogel composition which is able to form an anisotropic structure in vivo, after injection, comprising: (a) anisometric, i.e. rod or disc shaped, micro-elements that contain magnetic particles, particularly superparamagnetic iron oxide nanoparticles, and (b) a crosslinkable aqueous polymer formulation, in which such micro-elements are dispersed. The colloidal formulation can be injected as a colloidal liquid into a living body, respectively into an injured or diseased tissue, and the anisometric micro-elements can subsequently be aligned by applying a magnetic field with strength of less than 1.5 Tesla. Orientation of the anisometric micro-elements by an external magnetic field is enabled by proper choice of their geometric dimensions, their concentration, and the arrangement of the superparamagnetic iron oxide nanoparticles within these microelements. Subsequent in vivo crosslinking of the dispersing liquid results in a heterogeneous gel consisting of oriented microdomains of the micro-elements and an isotropic hydrogel matrix, formed by the crosslinked polymer solution, in which the anisometric micro-elements have been dispersed before injection. The matrix is typically chosen to be softer than the included oriented anisometric disc or rod-shaped micro-elements. The dispersed microelements are either small hydrogel bodies themselves or short polymer micro fibers.

The hydrogel formulations are designed to be employed by minimal invasive application for the treatment of soft and super soft damaged tissues, for example spinal cord injury (central nerve tissue is characterized by a modulus in the range of 0.2-7 kPa), myocardial infarction, stroke, cartilage injury or wound healing, which causes specific difficulties for surgical invasion. Different to hard implants from metals, ceramics or solid polymers, the main function of these soft hydrogels is not to support the structural strength of the respective tissue or organ, but to allow invasion of endogenous cells and support growth of the surrounding healthy tissue to repair the damaged tissue. Moreover, the hydrogel can be mixed with cells, which can be tissue-specific or stem cells, differentiable into any kind of cell, to regenerate the injured tissue. The oriented micro-elements provide a scaffold for tissue regeneration and are designed to mimic distinct functions of the extracellular matrix of the respective tissue. It is the key feature of this invention that the ingrowth of endogenous cells and the regeneration of tissue can be guided in an oriented way, while at the same time the application is as minimal invasive as possible, i.e., by injection through a pinhole as provided by a hollow needle. In a further aspect of this invention the soft anisotropic, in situ forming hydrogels can be further equipped with biological functions by means of incorporating specific biomolecules, in particular peptides, glycans and proteins that are part of the extracellular matrix, which can improve the healing effect further. These are typically paracrine signals like growth factors, but also peptide segments or glycans within the gel structure that can bind such paracrine signals or serve as cell adherent ligands or which can be degraded, e.g., by metalloproteases, to allow cell invasion and rearrange the gel structure to substitute it by natural extracellular matrix.

So far, several reports have shown the potential of soft implantable and injectable hydrogels to support tissue regeneration and to induce healing. It is, however, common to these findings that they cannot provide the combination of a minimum invasive application by injection in combination with a macroscopic orientation, as it is often needed for functional tissue regeneration. This combination of minimum invasive and generation of an anisometric scaffold is of special importance for spinal cord regeneration, where nerve guiding in combination with the preservation of the highly sensitive and fragile residual nerve function is mandatory.

Accordingly, the present invention particularly relates to an injectable, anisotropically alignable hydrogel composition comprising:
(a) soft, anisometric elements selected from magnetoceptive microgels (small hydrogel bodies) having a young modulus in the range of 10 Pa-50 MPa, preferably 1 kPa-50 MPa and comprising magnetic particles, particularly superparamagnetic iron oxide nanoparticles, and
(b) a crosslinkable biocompatible matrix hydrogel composition comprising said anisometric elements, wherein the anisometric elements are embedded and distributed within the matrix hydrogel composition.

The composite (hybrid) hydrogel according to the present invention is composed of soft magnetoceptive microgels (small hydrogel bodies) which are incorporated into a surrounding crosslinkable soft biocompatible matrix hydrogel composition. Here, the anisotropically alignable structures are not formed by magnetic particles, but oriented by the incorporation of a low concentration of magnetic particles, particularly superparamagnetic iron oxide nanoparticles, inside the anisometric elements, i.e. magnetoceptive microgels, which reduces iron cytotoxicity, avoids direct contact of the cells with a large concentration of iron. Depending on the tissue, the composite hydrogels can be designed to be degradable, supporting clearance from body, or non-degradable to assure the permanent tissue support. As the magnetic nanoparticles are here used to orient larger anisometric elements made of a non-magnetic material, i.e. the microgels, with controllable dimensions, stiffness, and structure, instead of forming the strings themselves as performed in Kim et al. and Antman-Passig et al., as cited hereinabove, the amount of iron oxide used is significantly reduced, which is favorable for in vivo applications.

The anisometric elements, i.e. magnetoceptive microgels, are mainly composed of water and doped inside with small amounts of said magnetic particles, particularly superparamagnetic iron oxide nanoparticles (SPIONs), which enables them to align within low magnetic fields in the milli-Tesla range. Furthermore, the microgel orientation is interlocked within the surrounding biocompatible matrix hydrogel, once crosslinked, thereby fixing the structural anisotropy (FIG. 1).

According to the present invention, typically, the magnetic particles, particularly superparamagnetic iron oxide nanoparticles, have a mean particle size in the range of 1 to 50 nm, measured by TEM and/or light scattering.

The magnetic particles, particularly superparamagnetic iron oxide nanoparticles, are embedded within said microgels by mixing in solution before crosslinking.

The length of the anisometric elements, i.e. magnetoceptive microgels, is typically in the range of 0.5-200 µm, preferably 10-120 µm. Their diameters can be in the range of 0.3-20 µm, preferably 1-5 µm. The microgels employed in the present invention can have an aspect ratio of 1.5 or higher, preferably 10 or higher.

The crosslinked microgels, which function as barriers, are soft, i.e. their young modulus is in the range of 10 Pa-50 MPa, preferably 1 kPa-50 MPa, more preferentially 10 kPa-5 MPa.

The crosslinked matrix hydrogel after injection has a young modulus in the range of 50 Pa-100 kPa, preferably 50 Pa-10 kPa to enable nerve growth.

To measure the young modulus and water content of the microgels, hydrogel disks with the same polymer composition were made. For mechanical characterization, hydrogel disks were subjected to unconstrained compression at room temperature using a Dynamic Mechanical Analysis (DMA) device (Q800 DMA, TA Instruments) equipped with a submersion clamp. The elasticity modulus was calculated from the slope of the linear region of stress-strain curves, obtained by applying a force ramp of 1N/min towards the samples.

To quantify the water content, the weight of the hydrogel disks was measured at room temperature in a water swollen state and after drying for 24 h at 40° C. The dry weight was then subtracted from the swollen weight to determine the amount of water. The water content should be between 70 and 99%. This enables diffusion of molecules through the structure.

In a preferred embodiment of the present invention, the superparamagnetic iron oxide nanoparticles are present inside the anisometric elements in an amount of 0.0001 to 10 vol.-%, preferentially 0.001 to 2 vol.-%, more preferentially 0.001 to 1 vol.-%, in terms of the anisometric elements. The anisometric elements are present in the injectable hybrid hydrogel composition in an amount of 0.01 to 40 vol.-%, preferably 0.1 to 10 vol.-%, more preferably 1 to 3 vol.-%, in terms of the hydrogel.

The matrix hydrogel composition can be selected from any suitable biocompatible hydrogel composition, which can subsequently be crosslinked into a soft matrix in the range of 50 Pa-100 kPa, preferentially 50 Pa-10 kPa, thus yielding a real hydrogel.

The matrix hydrogel/microgel materials can be selected from molecules, which are at least partly soluble in aqueous solutions, and can be derived from:

(i) natural components, which include, but are not limited to fibrinogen, collagens, cellulose, glycans, Matrigel, (self-) assembling peptides or proteins, ribonucleic acids, desoxynucleic acid, albumins, antibodies and fragments thereof, blood plasma protein, gelatin, alginates, elastin, fascin, keratins, polyaspartate, polyglutamate, prolamins, transferrins, cytochromes, flavoprotein, glycoproteins, hemoproteins, lipoproteins, metalloproteins, phytochromes, phosphoproteins, opsins, agar, agarose, arabinans, arabinogalactans, carrageenan, chitin, cellulose, carbomethyl cellulose, hydroxypropyl methylcellulose and other carbohydrate-based polymers, chitosan, dextran, dextrin, gelatin, hyaluronic acid and derivatives, mannan, pectins, rhamnogalacturonans, starch, hydroxyalkyl starch, xylan, (ii) synthetic components, which can be in linear, branched, dendrimeric, circular, or star shape or a combination of thereof, and which include, but are not limited to the group of polyvinyl-based polymers, like poly(vinyl acetate), poly(vinyl alcohol), poly(vinyl acetale), poly (vinyl ether), poly(vinyl pyrrolidone), poly(vinyl amines), and poly(vinyl methylether), the group of poly(meth) acrylates, like polyacrylic acid, polyacrolein, polyacrylnitril, poly(cyanoacrylate), poly(acrylamide), poly (N-isopropyl acrylamide), poly(dimethylacrylamide), poly (hydroxypropyl-methacrylamide), poly (methylmethacrylate), poly(methacrylate), and poly (hydroxyethyl acrylate), the group of poly(oxymethylene)s, the group of polyethers, like poly(ethylene oxide), poly(propylene oxide), poly(tetramethyl oxide), poly (phenylene oxide), poly(ethylene glycol), poly(propylene glycol), and poly (vinyl methyl ether), the group of polycarbonates, like poly(trimethylene carbonate), poly (orthocarbonate), and poly(iminocarbonates), the group of polyesters, like poly(3-hydroxybutyrate), poly(glycolic acid), poly(maleic acid), polydioxanones, poly(propylene fumarate), poly(anhydrides), the group of polyamides, like poly(imino carbonates), poly(amino acids), and poly (aspartamide), the group of carbon/sulfur based polymers, the group of silicones like polysiloxane, and polydimethylsiloxane, the group of polyurethanes, the group of polyimides, like poly(succinimide), poly(bis-maleine imide), poly(oxa-diazo-benzimidazole), poly(imide sulfone), and poly(methacryl imide), the group of phosphorous based polymers like phosphoesters (polyphosphates, polyphosphonates), and polyphosphazenes (poly [di(carboxylatophenoxy)phosphazene], poly[di (methoxyethoxyethoxy) phosphazene]), the group of polyoxazoline, like poly(2-alkyl-2-oxazolines), poly(hydroxypropyloxazoline), and poly(hydroxyethyloxazoline), and any polyelectrolyte of the aforementioned polymers;

(iii) co-polymers, which can be alternating, statistical, periodic, or block or a combination of thereof, and which consist but are not limited to any of the aforementioned aqueous-soluble polymers conjugated to another aqueous-soluble polymer or water-insoluble monomers, pre-polymers, or polymers, which include, but are not limited to poly($\varepsilon$-caprolactam), poly(caprolactone), poly(lactic acid), poly(glycolic acid), poly(ethylene succinate), poly (butylene succinate), polyvinylchloride, polybutadiene, polyisoprene, polychloroprene, poly(ethylene terephthalate), poly(phenyleneterephthalamide), poly(ether sulfone), as for instance co-polymers, like poly(3-hydroxybutyrate-co-hydroxyvalerate), poly(butylene adipate-co-terephthalate), poly(butylene succinate-co-terephthalate), poly(ethylene-co-vinyl alcohol), poly (ethylene-co-acrylic acid), poly(ethylene-co-maleic acid), poly(ethylene oxide)-co-poly(propylene oxide) block copolymers, polyether imide, poly amid imide, divinyl ether-maleic anhydride (pyran) copolymer, N-(2-Hydroxypropyl) methacrylamide (HPMA) copolymers, polyacrylic acid copolymers, polylactic-co-glycolic acid, polyethylene oxide-co-polypropylene oxide, co-polyethylene oxide block or random copolymers, copolymers of poly(hydroxy acid)s, poly(orthocarbonate)s, poly(anhydride)s, poly(lactone)s, poly(aminoacid)s, poly(carbonate)s, and poly(phosphonate)s.

Typically, different materials are used for matrix hydrogel and microgel. However, alternatively, the material for the matrix hydrogel and the microgel can be the same, provided that they differ in the crosslinking degree, e.g. by adopting different crosslinking methods, and/or stiffness.

In particular, hydrogel compositions from natural (fibrinogen, collagen, gelatin, alginate, hyaluron, cellulose, Matrigel, glycans) and the above given synthetic polymers as well as a combination of these can be used. Synthetic polymers particularly include hydrophilic polyethylenegylcol (PEG), polyglycidol, polycarbonates, polyoxazolines and their copolymers, as well as hydrophilic poly($\alpha$-olefines) from acrylates, methacylates, vinylphosphonates and vinylamides (e.g., vinylformamide, vinylacetamide, vinylpyrrolidon, vinyl-$\varepsilon$-caprolactam). Furthermore, the synthetic polymers, to be used for the matrix formulation include step-growth or polycondensation products such as hydrophilic polyurethanes, polyesters, polyamides, polyphosphates, and polyanhydrides as well as hydrophilic polysiloxanes obtained from equilibration reactions. Specific, non-limiting examples of a polyanhydride include one or more of poly(sebacic acid), poly(adipic acid), poly(terephthalic acid), and combinations thereof. Specific, non-limiting examples of a polyamide include one or more of poly(imino carbonates), polyaminoacids, peptides, and combinations thereof. Specific, non-limiting examples of a phosphorous-based polymer include one or more of a polyphosphate, a polyphosphonate, a polyphosphazene, and combinations thereof.

Particularly usable are poly (ethylene glycol) (PEG) and combinations of PEG and poly(propylene glycol), being poly(ethylene oxide-stat-propylene oxide). Particularly useful are polymers and oligomers that undergo selfassembly to gel structures by hydrogen bonding, hydrophobic interaction or coacervation of polyelectrolyte segments as it is typical for the natural materials like fibrinogen, collagen, gelatin, alginate, hyaluron, cellulose, Matrigel and well known for urethane and urea segments as well as for $\beta$-sheet and coiled-coil forming peptides.

In situ crosslinking is achieved by employing an aqueous polymer solution whose components undergo crosslinking sufficiently slowly so that they can be mixed together in an aqueous buffer as a solvent and also the anisometric hydrogel bodies can be dispersed homogeneously into this solution with sufficient time before gelation. The rate of the crosslinking reaction is adjusted in order to leave sufficient time for the injection and orientation of the anisometric micro-elements in a magnetic field that can be employed from outside. Crosslinking reactions are chosen not to interfere with the viability of the cells when the hydrogel formulation is injected. For covalent crosslink formation most preferred are Michael type addition reactions such as the addition of thiol and amine groups to vinylsulfon groups, acrylate groups or maleimide groups. Alternatively Thiol-En addition reactions and ligation reactions can be employed (D. P. Nair, M. Podgórski, S. Chatani, T. Gong, W. Xi, C. R. Fenoli, C. N. Bowman. The Thiol-Michael Addition Click Reaction: A Powerful and Widely Used Tool in Materials Chemistry. *Chem. Mater.*, 26 (1): 724-744 (2014); C. E. Hoyle, C. N. Bowman. Thiol-Ene Click Chemistry. *Angewandte Chemie Int. Ed.* 49: 1540-73 (2010); B. H. Hu, J. Su, P. B. Messersmith. *Hydrogels cross-linked by native chemical ligation. Biomacromolecules* 10(8):2194-200 (2009)).

In an alternative embodiment of this invention in vivo crosslinking is achieved by physical interactions such as hydrogen-bonding and hydrophobic interaction. This is of particular importance for the natural gel-forming polymers such as fibrinogen, collagen, gelatin, alginate, hyaluron, cellulose, Matrigel but also for gelation of selfassembling peptides (J. J. Rice, M. M. Martino, L. De Laporte, F. Tortelli F*, P. S. Briquez, J. A. Hubbell. Engineering the regenerative microenvironment with biomaterials. Advanced Healthcare Materials, 2(1): 57-71 (2013)).

According to the present invention, the anisometric elements and the matrix hydrogel can degrade overtime to be replaced by newly formed tissue. The degradation can be controlled by incorporating hydrolysable or enzymatically degradable domains (J. J. Rice, M. M. Martino, L. De Laporte, F. Tortelli F*, P. S. Briquez, J. A. Hubbell. Engineering the regenerative microenvironment with biomaterials. Advanced Healthcare Materials, 2(1): 57-71 (2013)).

In the context of the present invention, the term "anisometric microgel" stands for an already crosslinked microgel, i.e. the microgel is formed by a suitable microgel composition which is then cured/cross-linked by appropriate measures like e.g. UV curing, etc. The anisometric microgel can, for instance, be in rectangular form, rod-shaped or ellipse-like.

The microgels used in the present invention can be produced via any methods including single or multi steps such as electrospinning, microfluidics, lithography, Particle Replication in Non-wetting Templates (PRINT®), emulsion polymerization, precipitation polymerization, stretching, 3D printing, nanoscribing, etc.

According to an embodiment of the present invention, anisometric microgels are produced with a mold-based soft lithography approach, based and adopted from PRINT®, which has been developed and commercialized by DeSimone (Liquidia Tech. Inc.); cf. also New J. Phys. 2009, 11, 075018. Preferably, the anisometric microgels have a polymer weight to volume content less than 30% (FIG. 3), which represents an adequate range of polymer concentrations for in vivo purposes. The polymer content will determine the stiffness and structure of the gel, which will affect cell behavior, permeation of nutrients and cell signaling molecules, and the degradation of the microgels. Thus, preferably, the polymer content is within the range of 1 to 30%.

Figure 3:
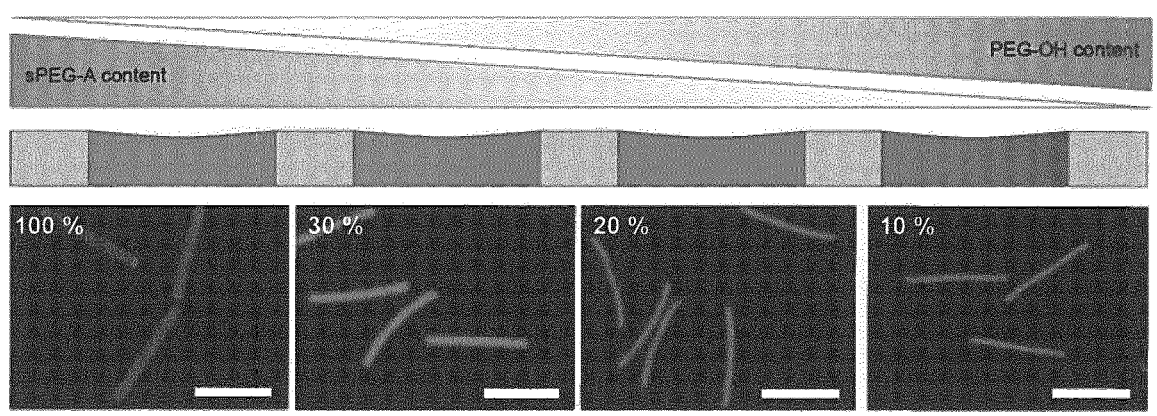

The rest volume of the final microgels mixed within the matrix hydrogel should be water. Here, the PRINT technique is adopted to obtain such anisometric microgels with controllable stiffness, structure, and mesh size, up to macroscopic pores to enhance permeation of molecules. Instead of water, a non-reactive higher molecular weight compound can be premixed with the crosslinking compound to induce phase separation while crosslinking and micro-heterogeneity, allowing better permeation through the microgels. This higher molecular weight compound facilitates anisometric microgel production by avoiding evaporation and maintaining the microgel composition during crosslinking and microgel fabrication. The non-reactive higher molecular weight compound enables sufficient filling of the predefined cavities in the replication mold, without increasing the final amount of crosslinked polymer inside the microgels. This non-reactive compound did not participate in the crosslinking mechanism and is easily washed out, replacing the void structures with an aqueous solution, and rendering soft microgels in the range of 1 kPa-50 MPa, preferentially 10 kPa-5 MPa, before mixing them inside the matrix hydrogel solution. The mixed SPIONs mainly retain inside the reactive polymer phase of the microgels, resulting in high encapsulation efficiencies, without significant SPION loss during removal of the non-reactive compound. Thus, in accordance with the present invention, the final anisometric soft microgels contain over 70% water, SPIONs distributed inside the polymer structure, and a microheterogenous structure (FIG. 3).

Different fluid non-reactive compounds, based on e.g. poly(ethylene glycol) (PEG-OH), polyglycidols or six-armed, star-shaped poly(ethylene oxide-stat-propylene oxide) (sPEG-OH) can be used, resulting in precise molding.

As an illustrative example of the present invention, six-armed, star-shaped poly(ethylene oxide-stat-propylene oxide) with acrylate end groups (sPEG-A) has been applied. The pre-polymer exists as a liquid due to the presence of 20% propylene oxide. sPEG-A is cast over a perfluoropolyether (PFPE) mold at different dilutions in the presence of a photoinitiator, using a polyethylene terephthalate (PET) sheet. UV-crosslinking of the solution filled features results in precisely replicated microgels with dimensions between 1-500 μm, which are harvested using a sticky polyvinylpyrrolidone layer, which can be dissolved by the addition of water (FIG. 2A, 2B). Diluting the PEG pre-cursor solution with water or other solvents, such as DMSO, can result in insufficient filling of the cavities due to evaporation of the fluid during crosslinking, causing deformed or incomplete microgels. This results in harvested microgels with a convex-shape when 20-75% sPEG-A is diluted in water, or two triangular microgels below 20% sPEG-A. Only above 75% sPEG-A, the template is replicated sufficiently well. The aim is to generate soft, permeable micro-heterogeneous, anisometric microgels with high shape fidelity and low polymer (<30 w/v %) contents, which enables more rapid in vivo degradability, less exposure to degradation products, and improved transport of nutrients and cell signaling molecules through the microgels. Therefore, the original technique has been refined by blending sPEG-A with a non-reactive second compound to enable sufficient filling of the cavities, without increasing the crosslinking density and final polymer content of the microgels. Different non-reactive compounds, based on poly(ethylene glycol) (PEG-OH) or six-arm, star-shaped poly(ethylene oxide-stat-propylene oxide) (sPEG-OH) can be used, resulting in precise molding. Microgels have been fabricated with a sPEG-A content down to 10% (FIG. 3), which represents an adequate range of polymer concentrations for in vivo applications.

Figure 4:
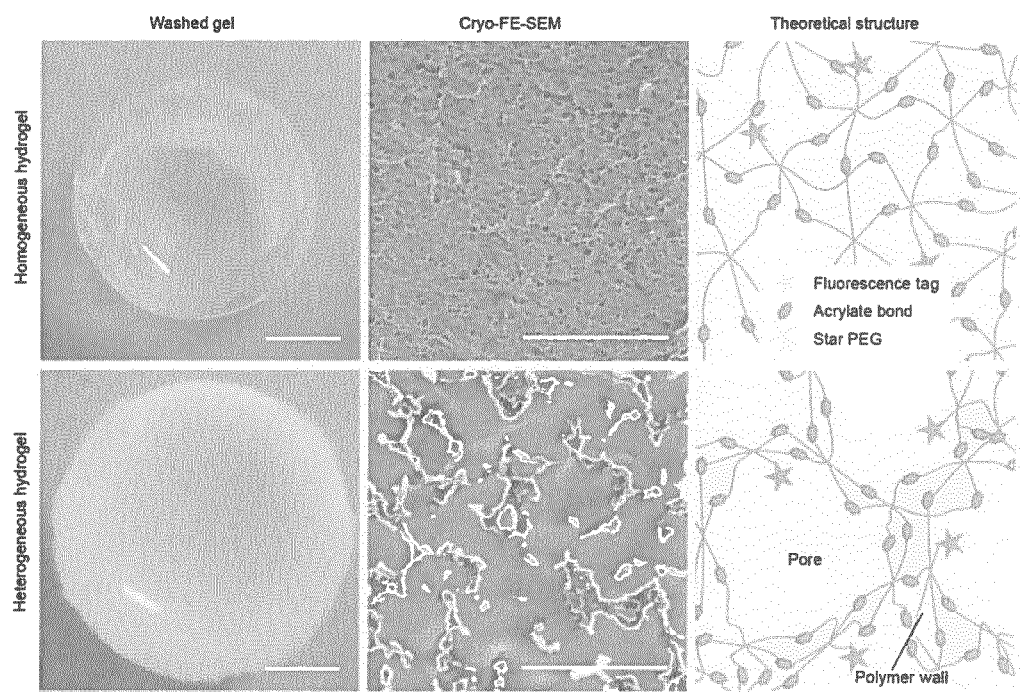
Figure 5:
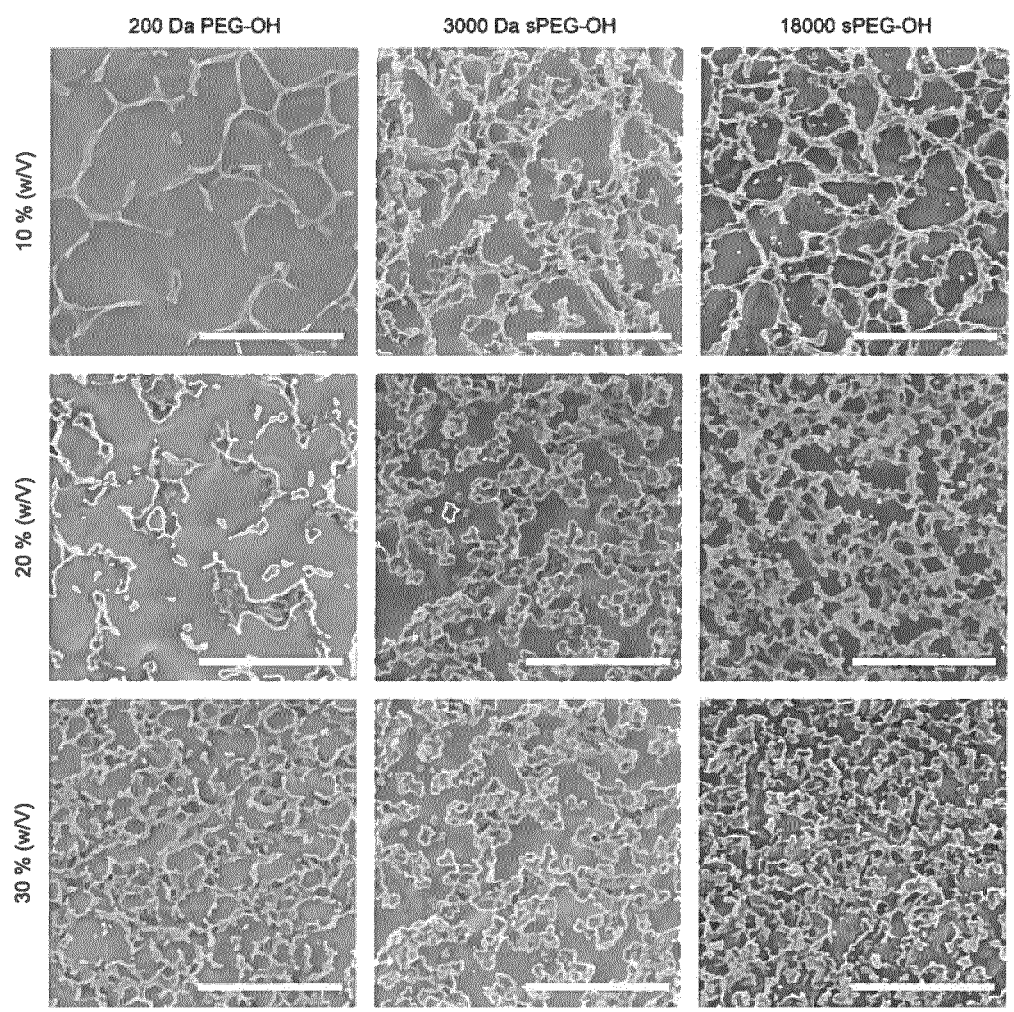

Importantly, the optional addition of the non-reactive compound during microgel fabrication induced reaction instability, as polymer blends tend to phase separate. To characterize the effect of different non-reactive compounds and their molecular weights (MW) on the microgel structure and mechanical properties, macroscopic hydrogel discs (12×1 mm) have been prepared with the same material compositions. The applied non-reactive compounds are PEG-OH 0.2 kDa, as well as sPEG-OH 3.0 kDa and 18.0 kDa, all existing in a liquid form. All non-reactive compounds are extracted rapidly within three times 30 minutes, as the dry weight of the hydrogels matched the theoretical dry weight of crosslinked sPEG-A, without significant loss of the SPIONs during the washing steps. After curing and extraction, microgels (hydrogels) fabricated with non-reactive compounds have a completely white appearance, in contrast to transparent microgels (hydrogels), fabricated with water (FIG. 4). Visualization of the microscopic appearance of cross-sections of generated microgel (hydrogel) disks by cryo-FE-SEM reveals a clear porous structure up to micrometer scale, which can be reduced by increasing the sPEG-A content and varying the applied non-reactive compounds (FIG. 5). Moreover, cryo-FE-SEM, as well as cryo-cutting and subsequent FE-SEM measurements show two different morphological appearances in the case of low MW PEG-OH and high MW sPEG-OH non-reactive compounds (FIG. 6A). Both sPEG-OH non-reactive compounds (3 and 18 kDa) lead to a more coarse granular structure with smaller globuli for sPEG-OH 18.0 kDa, whereas the lower MW non-reactive compound shows a more microscopic mesh structure, which may explain why higher MW sPEG-OH non-reactive compounds result in softer, more swellable gels.

Another characteristic feature of the microgels, fabricated with non-reactive compounds, lies in their significantly higher swelling ratio and water uptake, compared to microgels (hydrogels) fabricated with water with the same amount of sPEG-A (FIG. 6B). Correspondingly, the elastic modulus is lower for microgels, fabricated with non-reactive compounds, than for microgels fabricated with water with the same amount of crosslinked polymer (FIG. 6C). An exception is 30% sPEG-A hydrogels, fabricated with PEG-OH 0.2 kDa as non-reactive compound, which have a similar modulus as the water-diluted variant. The addition of the non-reactive compound during microgel fabrication enables variation of the internal structure, mesh size, stiffness, and swelling, without changing the MW and concentration of the reactive polymer phase. Based on the findings above, blending the non-reactive compound within the reacting sPEG-A phase creates a micro-heterogeneous structure, which consists of nano-porous polymeric parts and large voids up to a few micrometers (FIG. 4, 6A). Mechanistically, the two polymers are phase-separating during crosslinking of the reacting phase, which is a well-known phenomenon, called reaction-induced phase decomposition (RIPD). The conformational entropy reduces as the MW of one blend component increases, which causes an increase of the Gibb's free energy ($\Delta G$), inducing phase separation. In addition, it can be confirmed that the crosslinked network chains are incompatible with the non-reactive compound by incubating the dried microgel within the non-reactive compound. No swelling is observed, whereas the dried microgels swelled rapidly in water, supporting the RIPD-hypothesis.

When comparing the swelling degree and elastic moduli among the different non-reactive compounds, it has been observed that the microgels, prepared with the low MW linear PEG-OH non-reactive compound, are significantly stiffer compared to the microgels, fabricated with the higher MW sPEG-OH non-reactive compounds. Even though this difference becomes more distinct for higher sPEG-A concentrations (20 and 30%), there is no significant difference in swelling among the non-reactive compounds at these concentrations. This is in contrast with conventional water-based hydrogels, for which an increasing elastic modulus is associated with less water uptake, which again supports the heterogeneity of microgel structures, fabricated with non-reactive compounds. For lower sPEG-A (10%), no significant differences in stiffness are observed between the different non-reactive compounds, while the swelling degree increases with reduced MW of the non-reactive compound. This may be explained by the presence of larger macroscopic pores for decreasing MW of the non-reactive compound (FIG. 5). The enhanced stiffness of microgels, fabricated with non-reactive compounds, i.e. the low MW PEG-OH non-reactive compound, may be due to their higher interconnectivity in comparison to the more globular structures of microgels, prepared with high MW sPEG-OH non-reactive compounds. This distinction between an interconnected and globular structure is intensified with increasing sPEG-A content (FIG. 5). These differences might be due to altered phase separation, as a spinodal decomposition is known to be more regularly interconnected, whereas a binodal decomposition characteristically consists of associated gel nuclei, giving it a more irregular globular structure. More interconnected polymer walls may be the reason for enhanced stiffness's without increased swelling behavior.

As the above described structural and mechanical properties can change with scale and fabrication method, microgels with a sPEG-A content of 20% and different non-reactive compounds are visualized by cryo-FE-SEM (FIG. 6A). The method reveals a similar heterogeneous appearance as the hydrogel disks with the respective porosity. Towards the direction of cell growth, microgels need to function as non-contact barriers or cell contact-guiding elements. In this example, synthetic microgels, not modified with biological domains, function in a non-cell-contact manner and align cells by being less soft than the surrounding matrix hydrogel and less favorable for cell infiltration, creating transient barriers and steric hindrance. By further modification of the microgels with biofunctional domains, such as ECM molecules or peptides, the microgels can be rendered cell adhesive. Generally, higher sPEG-A contents can achieve greater stiffness's, especially in hydrogels, fabricated with 0.2 kDa PEG-OH as non-reactive compound. However, as the microgels need to be cleared in vivo, microgels with a sPEG-A content of 20%, fabricated with 0.2 kDa PEG-OH, are chosen as first example.

To render the microgels magnetic, SPIONs are dispersed randomly inside the pre-polymer solution before molding and curing (crosslinking). By entrapping SPIONs inside the anisometric microgels, they are expected to obtain dipole interactions within a magnetic field and orient along the magnetic easy-axis, which mostly is dominated by the geometry of the microgels. By applying a sufficient magnetic field, and sufficient SPIONs inside the microgel, the SPIONs interact through long range dipolar interactions, inducing a net magnetization over the anisometric microgels' geometry.

As the non-reactive compound in the microgels is washed out before mixing inside the matrix hydrogel liquid, the incorporation efficiency and retention of SPIONs has been analyzed. Therefore, the iron content of macroscopic hydrogel disks has been determined by elemental analysis after washing, as well as the SPIONs released over time. SPIONs within a 20% sPEG-A hydrogel network, fabricated with PEG-OH 0.2 kDa as non-reactive compound, are fully retained, despite complete removal of the non-reactive compound (FIG. 7A). In comparison, hydrogels, fabricated with sPEG-OH as non-reactive compound, loose more than 20% of the SPIONs during washing. The difference might be attributable to the different RIPD mechanisms, in which the SPIONs may be better entrapped within the network over the progression of the reaction. After extraction of the non-reactive compound, it has been found that there is no significant release of SPIONs over a period of 4 weeks, which indicates a high SPION retention capacity of the hydrogel network (FIG. 7B). As a first example, microgels with 20 w/v % sPEG-A are applied using the PEG-OH 0.2 kDa non-reactive compound to obtain a sufficiently high persistence length, compared to the ultrasoft matrix hydrogel in the Pa-kPa range, and maximal SPION retention.

Transmission electron microscopy (TEM) reveals that dispersion homogenization via ultrasonication treatment yields well-dispersed SPIONs with few aggregates throughout the microgel (1 μm diameter and 10 μm length), which is required to achieve a uniform magnetic response (FIG. 7C). Elemental mapping verifies that the detected nanoparticles are composed of iron. Surprisingly, the randomly distributed nanoparticles inside the microgels lead to longitudinal alignment of the SPION-doped microgels (5 μm diameter, 50 μm length) in a magnetic field as low as 100 mT or lower (FIG. 7D). The minimal magnetic field required for alignment of SPION-doped (100 μg/mL (0.0011 v % SPIONs) and 400 μg/mL (0.0046 v % SPIONs), with 45.6% iron oxide content) microgels (5 μm diameter, 50 μm length) is 3.5 and 1.9 mT, respectively.

Both the magnetic response of the microgels and the gelation time of the surrounding matrix hydrogel need to be tuned to fix the microgel orientation and achieve optimal alignment without microgel accumulation close to the magnets. Fibrin can be chosen as a model for the biocompatible matrix hydrogel, and its gelation time is controlled to approximately 1 min by using a thrombin concentration of 0.125 U/mL to activate the fibrin pre-cursor fibrinogen in the clotting cascade. The orientation rate of the microgels is determined via a software-based orientation analysis through the ImageJ plugin OrientationJ, which evaluates every pixel of the image based on a structure tensor. A SPION concentration of 400 μg/mL is sufficient to align microgels in a magnetic field of 100 mT within 36.4±4.9 s (FIG. 7E, 7F). Increasing the SPION concentration to 1000 μg/mL, or increasing the magnetic field to 300 mT results in shorter orientation times. Interestingly, microgels with a concentration of 1000 μg/mL (0.011 v % SPIONs) in 300 mT start to move within the dispersion and interact with each other, causing aggregation and difficulties in the software-based orientation analysis. Microgels with 400 μg/mL SPIONs are selected to minimize the amount of SPION incorporation and eliminate cytotoxic side effects. These microgels are able to be fixed in their oriented state inside the fibrin matrix hydrogel, creating a global composite unidirectional anisotropy (FIG. 7G).

Cytotoxicity of the SPION-doped sPEG-A is tested in vitro by a cell viability assay, revealing no release of cytotoxic hydrogel components within 24 h. The hydrogel/media extract does not reduce cell survival or proliferation rates over a period of 5 days. To study the effect of microgels on cell morphology, microgel-fibrin composites with embedded L929 mouse-derived fibroblasts are injected into a glass-bottom PDMS well, which is kept within a magnetic insert of 130 mT for 10 min until completion of fibrin crosslinking. A concentration of 500 cells/μL gel is found most favorable to study fibroblast adhesion inside fibrin. A microgel concentration-dependent effect on fibroblast cytoskeleton elongation and orientation is found. A composite with 0.5 to 1.0 v % microgels shows fibroblast growth in all three dimensions, whereas an increasing concentration to 2.0 and 3.0 v % microgels leads to one dimensional growth along the microgel orientation (FIG. 8A). Thus, the higher the degree of material anisotropy, the stronger is the influence on cell orientation (FIG. 8B, C). As sPEG-A does not inherit cell adhesion sequences, an upper limit is assumed, above which cells cannot further adhere sufficiently to the matrix. The cells are therefore forced to attach to the fibrin gel, with the microgels functioning as barriers to induce cell orientation.

Figure 9:
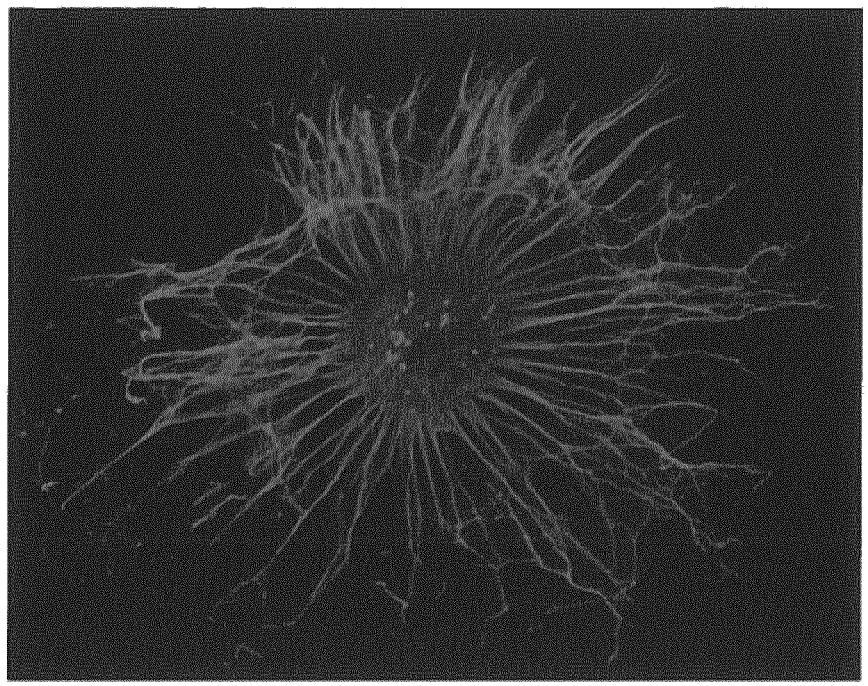

To investigate the materials functionality in regard to native oriented tissues, such as nerves, embryonic chick (10 days) DRGs (dorsal root ganglia) are inserted into the microgel-fibrin composites during the enzymatic crosslinking of the fibrin matrix inside a magnetic field. The constructs are cultured for 5 days and supplemented with nerve growth factor. In fibrin gels without microgels, neurites extended radially throughout the entire gel (FIG. 9). By adding non-oriented microgels, the neurites infiltrated the surrounding matrix strongly in the first 200 to 400 μm, where no microgels were present. This initial growth burst can be related to the experimental procedure of DRG insertion, creating a local region adjacent to the DRG with lower microgel and fibrin densities. When in contact with the non-oriented microgels, neurite infiltration into the hydrogel stagnated and their growth remained localized, ending with neurite bundle formation (FIG. 10A). A high propensity for neurite bundle formation has previously been related to poor substrate adhesion (J. W. Xie, W. Y. Liu, M. R. MacEwan, P. C. Bridgman, Y. N. Xia, Neurite Outgrowth on Electrospun Nanofibers with Uniaxial Alignment: The Effects of Fiber Density, Surface Coating, and Supporting Substrate. *Acs Nano* 8, 1878-1885 (2014)), which may also be the case for the randomly oriented microgels, creating a physical barrier. In case of 3 v % unidirectionally aligned microgels, similar observations can be made close to the DRG, while oriented neurite extension is observed in the presence of the aligned microgels (FIG. 10A). The physical barrier, created by the oriented microgels, supports linear neurite infiltration in the space between the oriented microgels, while blocking neurite extension perpendicular to the microgel orientation. Analysis of the structure of the complete DRG demonstrates the orientation distribution of the growing axons (FIG. 10B). Contrary to the reported results with fibroblasts, 1.0 v % microgels in fibrin is sufficient to orient neurite outgrowth, but axons are less straight and exhibit a more branched structure, compared to 3.0 v % (FIG. 10A). Consequently, microgels have the ability to align neurite outgrowth purely triggered by material anisotropy, confirming the applicability as an injectable composite hydrogel for the regeneration of oriented tissues.

While the hydrogel compositions according to the present invention can be used in any kind of industrial applications, which need in situ anisotropic architecture, like in electronic, textile, cosmetic, automobile, civil, aerospace, purification and filtering techniques, another subject matter of the present invention relates to the hydrogel composition described herein for use in medicine. In particular, the hydrogel composition according to the present invention can be used in the treatment of, but not limited for spinal cord injury, myocardial infarction, stroke, bone injury, cartilage injury or wound healing. Particularly, said composition is administered via injection to a site of treatment, matching its mechanical properties, and a magnetic field is then applied in order to anisotropically align the anisometric elements in a desired direction. Subsequently, the soft matrix hydrogel composition is cross-linked in order to fix the orientation of the soft anisometric elements as aligned by said magnetic field. Accordingly, after injection in vivo, by application of a magnetic field in the range of 0.1 mT to 1.5 T, typically in the milli-tesla range (100-600 mT), the magnetoresponsive anisometric elements are aligned to yield an anisotropic hydrogel structure. By crosslinking the matrix hydrogel, the orientation of the anisometric elements comprising the superparamagnetic iron oxide nanoparticles will be fixed after removal of the magnetic field. The distance between neighboring anisometric elements within the cross-linked matrix hydrogel is typically in the range of 0.1-100 µm, preferably 3-75 µm. For example, when fibrinogen is used as matrix hydrogel composition, crosslinking can be performed by adding thrombin in an amount sufficient to crosslink the matrix hydrogel composition.

The present invention further comprises incorporating one or more bioagents into the hybrid hydrogel or anisometric microgels. The one or more bioactive agents can, for example, be selected from cells, antibodies, cytokines, enzymes, thrombins, thrombin inhibitors, proteases, anticoagulants, heparins, growth factors, crosslinking inhibitors, matrix inhibitors, glycosaminoglycans, nucleotides, peptides, and antimicrobial agents.

Alternatively to the soft microgels addressed hereinabove, short flexible electrospun fibers with tailorable dimensions, stiffness, structure, and topography, having magnetic particles, particularly SPIONs, incorporated inside the fibers, can be used as anisometric elements. In the case of such short electrospun fibers as the anisometric elements, the magnetic particles, particularly superparamagnetic iron oxide nanoparticles, are embedded within said short electrospun fibers as well, by mixing in solution before spinning.

When adopting such short electrospun polymeric fibers as anisometric elements, non-limiting examples of polymers that may be used to form the polymeric fibers include (i) natural components, which include, but are not limited to fibrinogen, collagen, cellulose, Matrigel, (self-) assembling peptides or proteins, ribonucleic acids, desoxynucleic acid, albumins, antibodies and fragments thereof, blood plasma protein, collagens, elastin, fascin, keratins, polyaspartate, polyglutamate, prolamins, transferrins, cytochromes, flavoprotein, glycoproteins, hemoproteins, lipoproteins, metalloproteins, phytochromes, phosphoproteins, opsins, agar, agarose, arabinans, arabinogalactans, carrageenan, chitin, cellulose, carbomethyl cellulose, hydroxypropyl methylcellulose and other carbohydrate-based polymers, chitosan, dextran, dextrin, gelatin, hyaluronic acid and derivatives, mannan, pectins, rhamnogalacturonans, starch, hydroxyalkyl starch, xylan;

(ii) synthetic components, which can be in linear, branched, dendrimeric, circular, star shape or a combination of thereof, and which include but are not limited to the group of polyvinyl-based polymers, like polyvinylchloride, poly (vinyl acetate), poly(vinyl alcohol), poly(vinyl acetale), poly(vinyl ether), poly(vinyl pyrrolidone), poly(vinyl amines), and poly(vinyl methylether), the group of poly (meth)acrylates, like polyacrylic acid, polyacrolein, polyacrylnitril, poly(cyanoacrylate), poly(acrylamide), poly (N-isopropyl acrylamide), poly(dimethylacrylamide), poly(hydroxypropyl-methacrylamide), poly(methylmethacrylate), poly(methacrylate), and poly(hydroxyethyl acrylate), the group of poly(oxymethylene)s, the group of polyethers, like poly(ethylene oxide), poly(propylene oxide), poly(tetramethyl oxide), poly(phenylene oxide), poly(ethylene glycol), poly(propylene glycol), and poly (vinyl methyl ether), the group of polyesters, like poly (caprolactone), poly(lactic acid), poly(glycolic acid), poly (butylene succinate), poly(ethylene succinate), poly(3-hydroxybutyrate), poly(glycolic acid), poly(maleic acid), polydioxanones, poly(propylene fumarate), poly(anhydrides), poly(ethylene terephthalate), the group of polycarbonates, like poly(trimethylene carbonate), poly(orthocarbonate), and poly(iminocarbonates), the group of polyamides, poly(ε-caprolactam), poly(imino carbonates), poly(amino acids), and poly(aspartamide), the group of carbon/sulfur based polymers, like poly(ether sulfone), the group of silicones like polysiloxane, and polydimethylsiloxane, the group of polyurethanes, the group of polyimides, like poly(succinimide), poly(bis-maleine imide), poly(oxa-diazo-benzimidazole), poly(imide sulfone), and poly(methacryl imide), the group of phosphorous based polymers like phosphoesters (polyphosphates, polyphosphonates), and polyphosphazenes (poly[di(carboxylatophenoxy)phosphazene], poly[di(methoxyethoxyethoxy) phosphazene]), the group of polyoxazoline, like poly(2-alkyl-2-oxazolines), poly(hydroxypropyloxazoline), poly(hydroxyethyloxazoline), the group of polyaryles, like polystyrene, the group of polysilane, and others like polyisoprene, polychloroprene, polybutadiene, and any polyelectrolyte of the aforementioned polymers;

(iii) co-polymers, which can be alternating, statistical, periodic, or block or a combination of thereof, and which consist but are not limited to any of the aforementioned polymers.

In the course of the present invention, different types of spinning can be applied, such as needleless electrospinning, melt electrospinning, emulsion electrospinning, solution electrospinning, near field electrospinning, and any type of collector such as disc, drum, parallel plate, centrifugal, magnet assist can be used. To obtain short fibers, aligned fibers can be further cut using different strategies, such as ultrasonication, homogenizing, chemical treatment, standard razor blades, patterned UV-crosslinking, discontinuous electrospinning, or microsectioning.

As far as specific other parameters (amounts, SPION concentration, etc.) are concerned, the same is applicable as given hereinabove for the magnetoceptive microgels as anisometric elements.

In a preferred embodiment, electrospinning/microcutting is adopted to enable the production of relatively monodisperse flexible fibers (FIG. 11A and FIG. 11 D-E), which is crucial to control cell-fiber interactions and the effect of the fiber dimensions and aspect ratio on cell growth. This process involves the collection of aligned nano/microfiber mats via electrospinning, followed by embedment in a cryogel and a microsectioning step to convert the fiber mat into short cylindrical nano/microfibers with well-defined dimensions.

Figure 16:
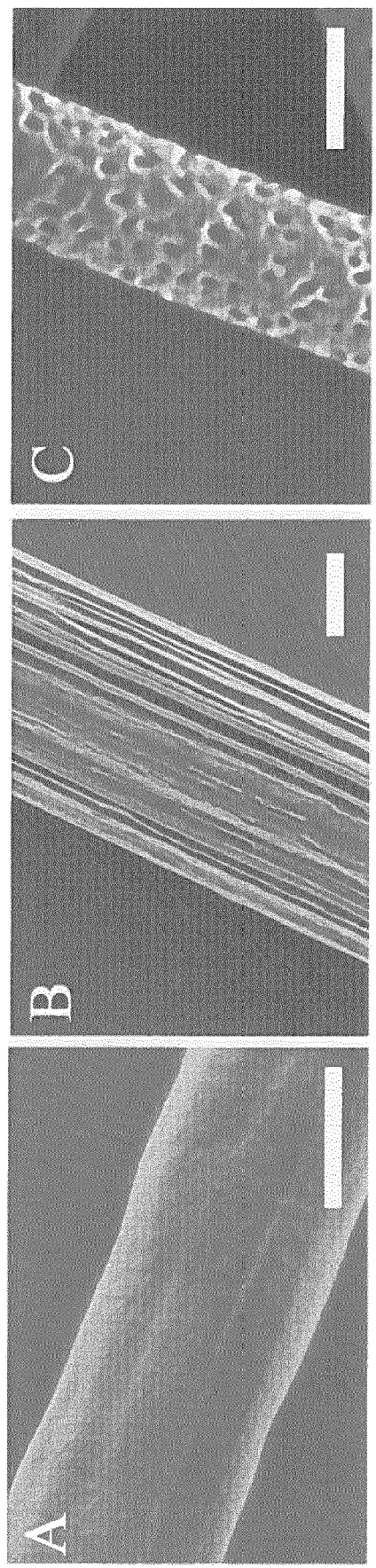

In the present invention, this method is adapted to produce, for example, short poly(lactide-co-glycolide acid) (PLGA) and poly(caprolactone) (PCL) fibers, incorporated with superparamagnetic iron oxide nanoparticles (SPIONs) inside the fibers. Accordingly, electrospun highly aligned fibers with submicron and micron diameters can be formed on, for example, a parallel plate type (FIG. 11B-C) collector or rotating drum (FIG. 17A-B). The short fiber lengths can be conveniently controlled by adjusting the slice thickness of a cryotome device. After dissolution of the embedment cryogel in water at room temperature, the short fibers are suspended in water of buffer. The physical dimensions of short fibers, such as their length and diameter, can be tuned by either adjusting the cryosectioning step and solution and electrospinning process parameters, respectively. The fiber surface morphology can be tuned by changing the solvent system properties and electrospinning ambient condition (i.e. temperature and humidity). Thus different surface topographies, such as smooth, porous and grooved can be achieved without any post treatments. Porous fibers are mainly formed due to the breath figures and the phase separation mechanisms. In the first mechanism, the solvent evaporation causes a lowering of the temperature on the surface of the filament. Water vapor from the atmosphere will condense on the surface, leaving an imprint on the fiber surface (FIG. 16 C). Grooved surface fibers are obtained due to the strong convection and instantaneous evaporation of solvent, resulting in voids that are initially formed on the jet surface at the early electrospinning stage; with elongation of the fiber and depending on the polymer's viscoelastic properties, the voids are highly stretched to form oriented lines on the fiber surface (FIG. 16 B) (C. Huang, Y. Tang, X. Liu, A. Sutti, Q. Ke, X. Mo, X. Wang, Y. Morsi, T. Lin, Electrospinning of nanofibres with parallel line surface texture for improvement of nerve cell growth. Soft Matter, 7, 10812, (2011)). In contrast, for solutions with less concentration and hence relatively low viscosity, smooth surfaces can be achieved after the evaporation of solvent from jet surface (FIG. 16 A).

Figure 13:
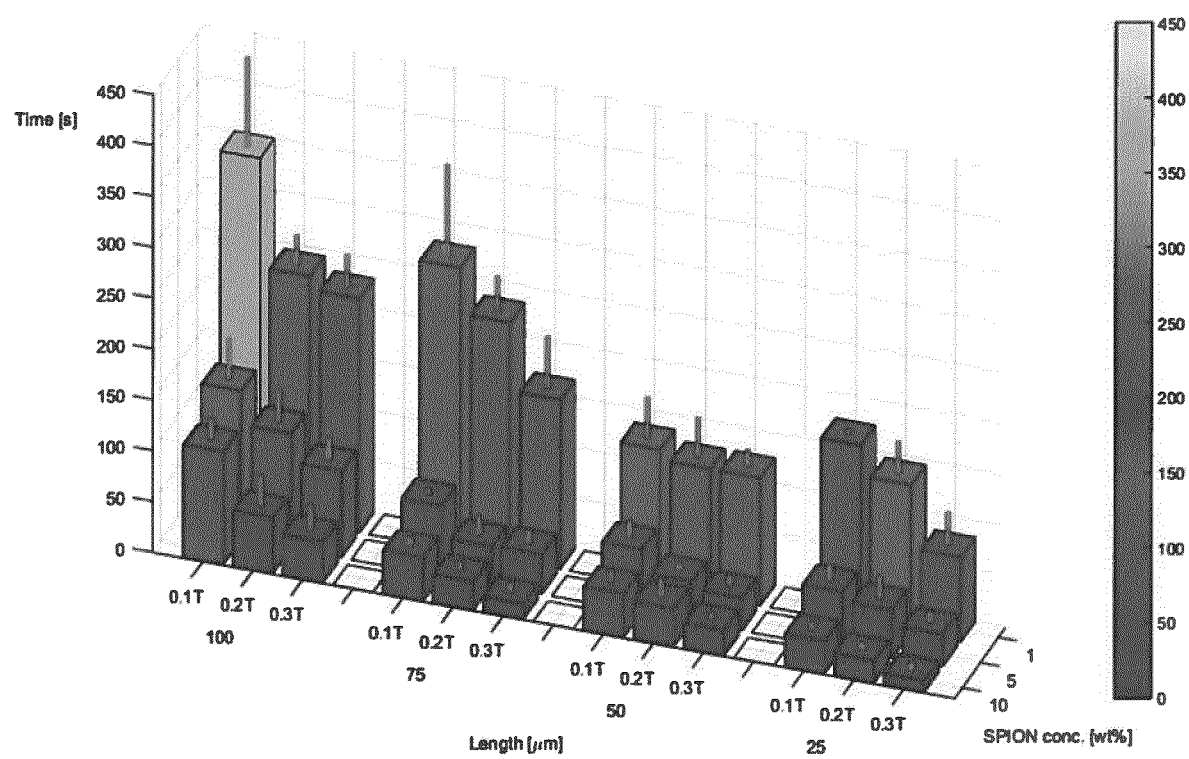
Figure 14:
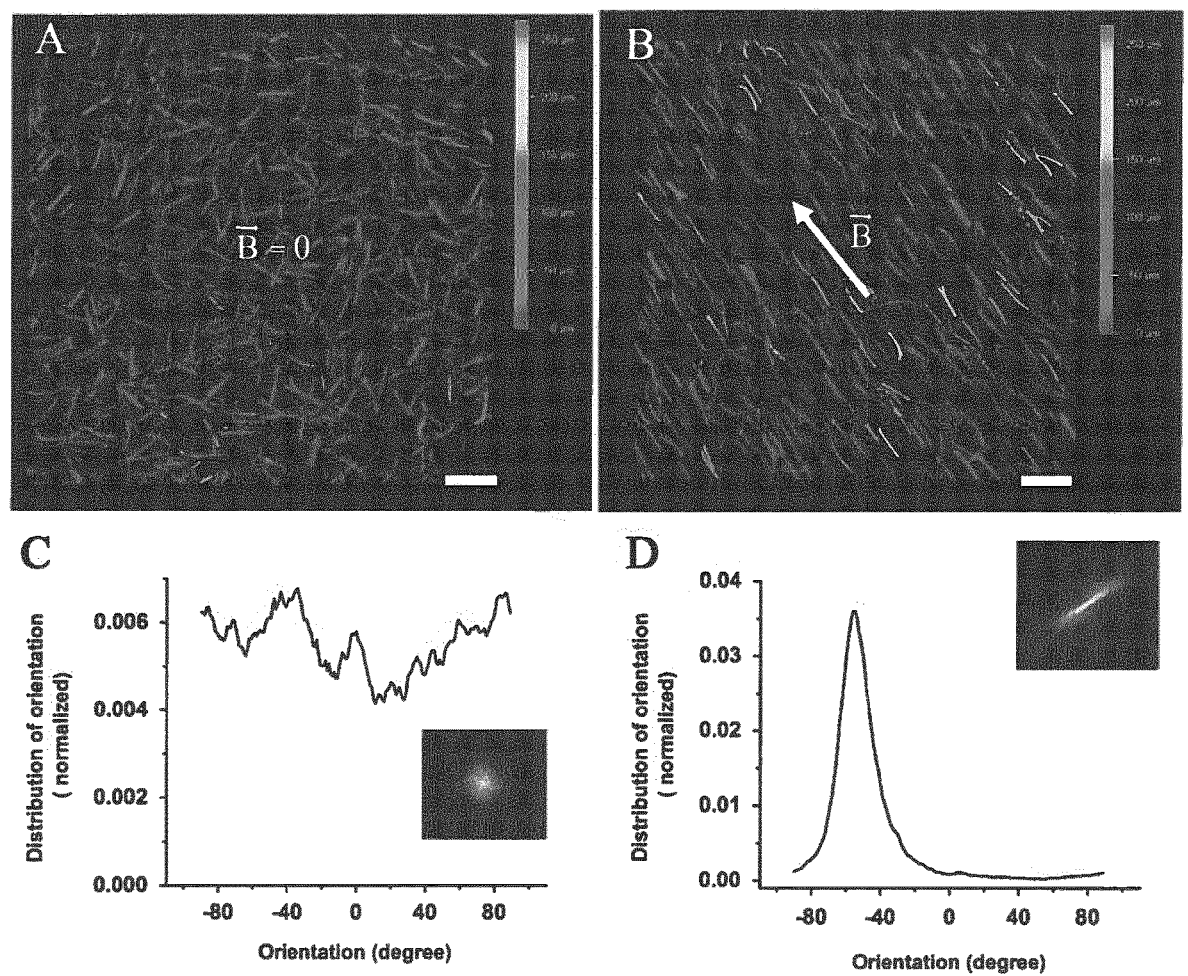
Figure 15:
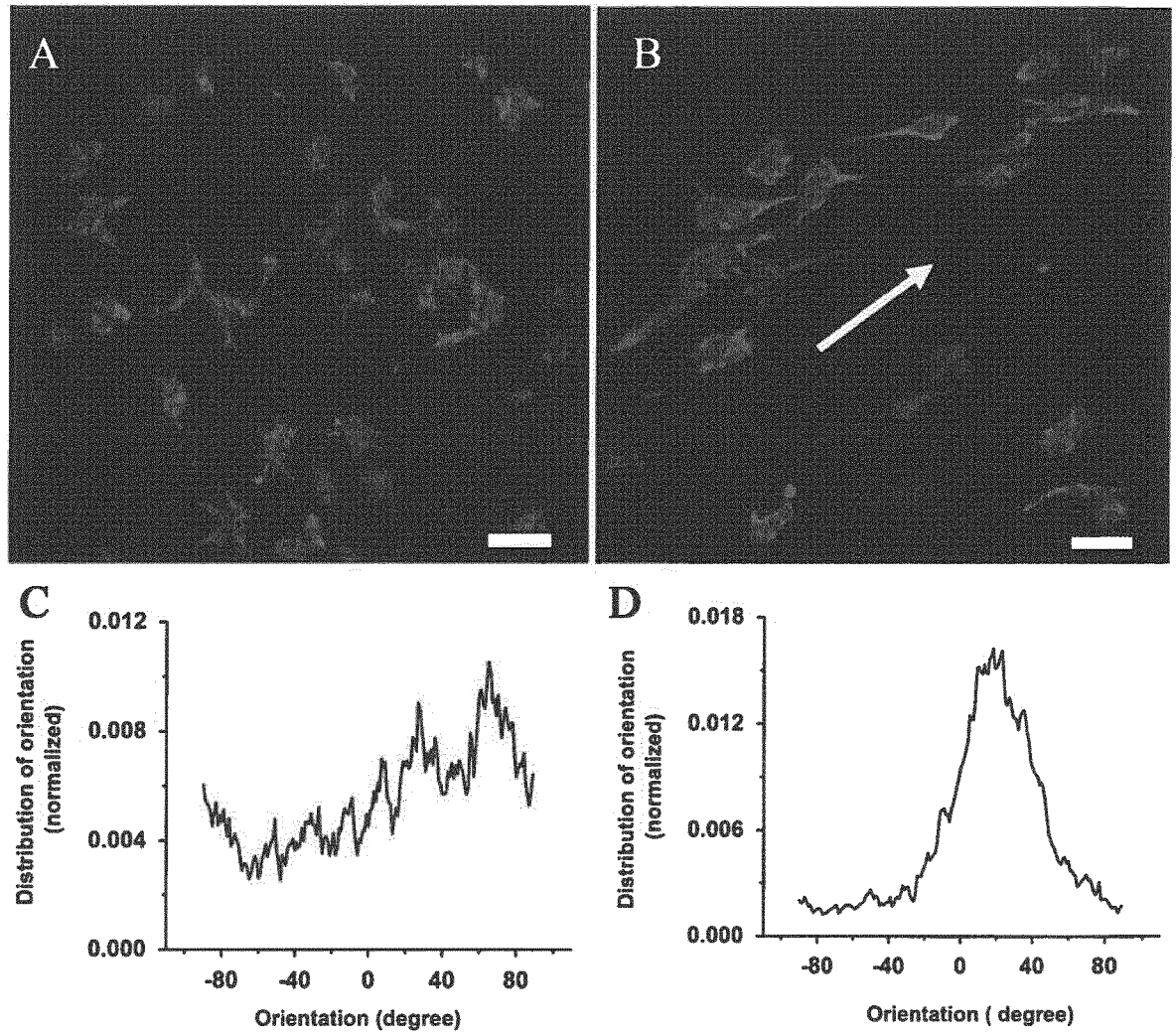
Figure 18:
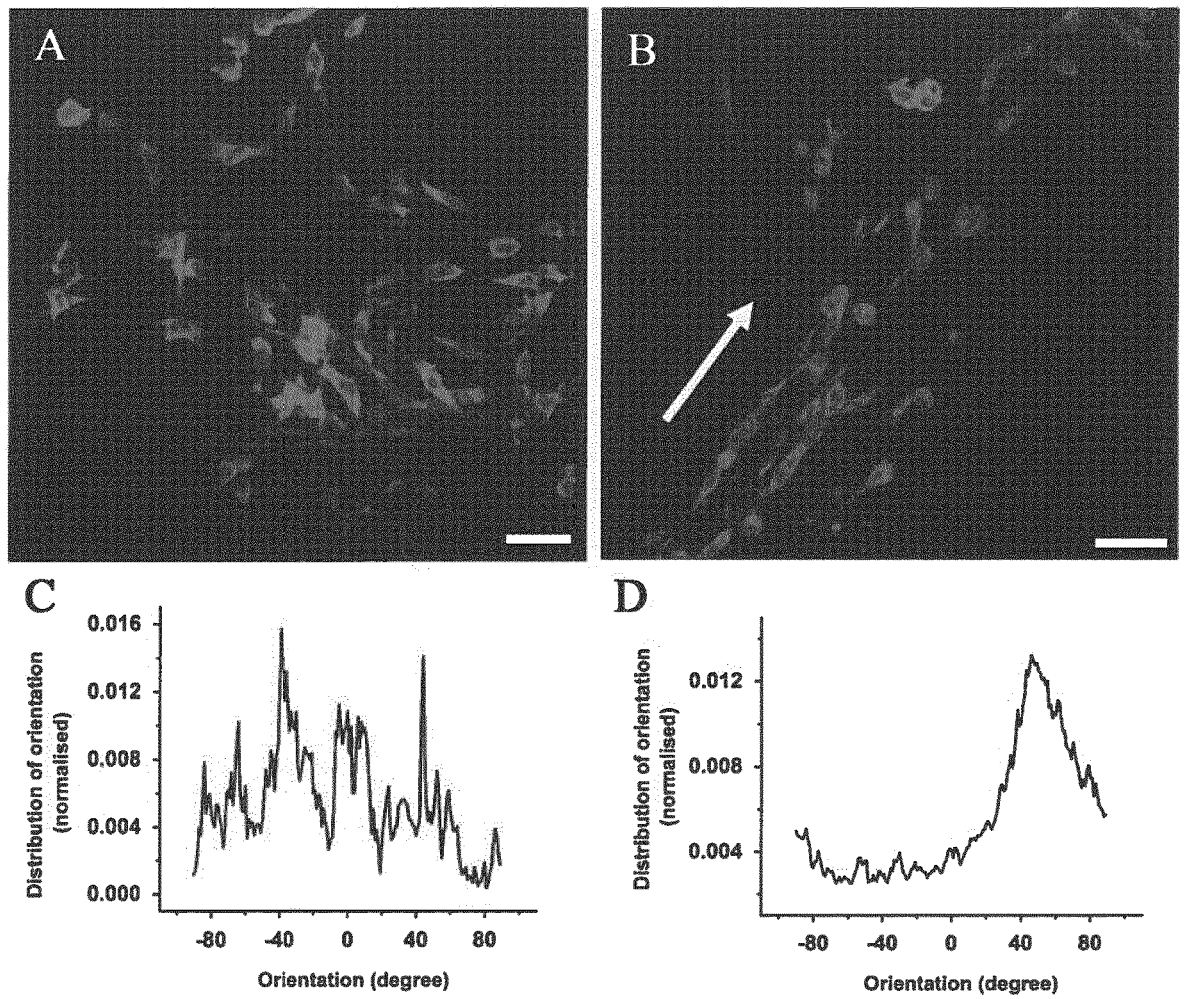
Figure 19:
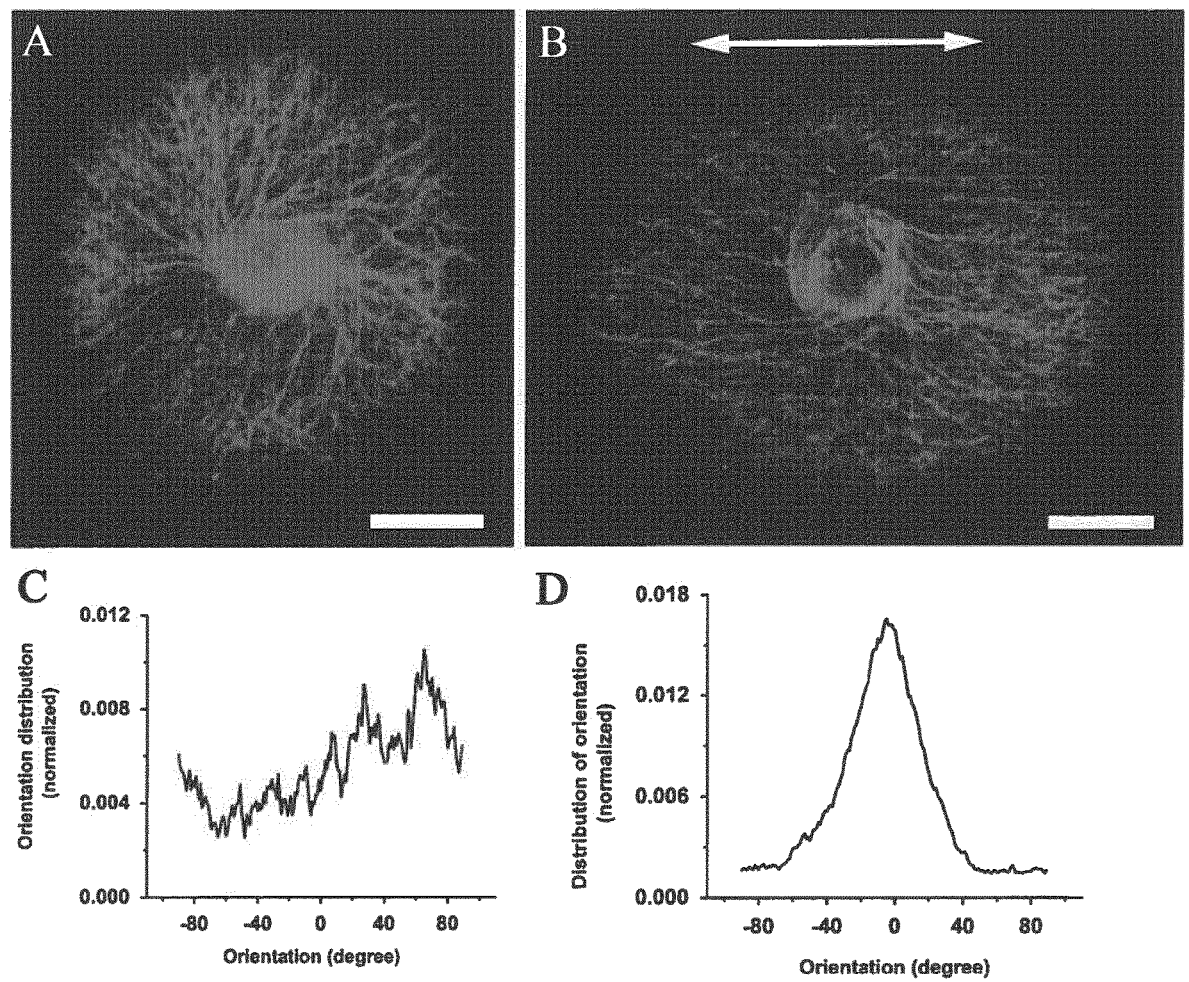

To render the microfibers magnetic, as an example, oleic acid capped synthesized SPIONs (FIG. 12A-B) were dispersed randomly in the polymer solution before the electrospinning process. The orientation time of the short fibers is affected by the amount of SPION encapsulated inside the fibers, the external magnetic field strength, and the length of the flexible fibers (FIG. 13). The orientation time of short magnetic PLGA fibers decreases with increasing SPION concentration and magnetic field strength, while increasing fiber lengths lead to slower orientation times. The short magnetic doped PLGA fibers (containing 4 w/v % Iron oxide) were mixed within a fibrinogen solution at a volume percentage of 0.015% in the presence of a low external magnetic field (300 mT), which leads to unidirectional orientation of the short fibers in the direction of the field, while the fibrinogen solution crosslinked around the fibers to form a fibrin matrix hydrogel and thus a hybrid hydrogel containing oriented fibers (FIG. 14). The oriented fibers are interlocked within the matrix hydrogel, which preserves the anisotropic architecture of the matrix after removal of the magnetic field. As an example, fibroblast cells, mixed together with the magnetic short fibers and the matrix pre-crosslinked hydrogel material, are injected in a mold, with subsequent fiber orientation and gelation of the matrix hydrogel in the presence of a magnetic field, and show linear growth in the direction of the aligned short fibers (FIG. 15). In the case of 0.3 v % unidirectionally aligned PCL fibers (containing 0.35 w/v % Iron oxide and with dimension of 5.2±0.97 nm) (FIG. 17 c-d), similar observations can be made regarding linear fibroblast growth (FIG. 18). The short PLGA and PCL fibers function as cell contact-guiding elements, as cells attach to and migrate along these fibers. Embryonic stage ten (E10) chick DRGs (dorsal root ganglia) were inserted into the composite fibrinogen-short fibers solution, while the fibrinogen was enzymatically crosslinking to fix the position of DRG and aligned fibers in direction of the external magnetic field. Oriented neurite extension is observed in the presence of the aligned PLGA short fibers, while DRG extensions in the gel with randomly oriented fibers were isotropically oriented in all directions (FIG. 19). The physical barrier, as well as contact cues created by the oriented short cell-adhesive fibers, support linear neurite infiltration in the space between and along the oriented short fibers. An initial growth burst can be seen in both cases, while in the case of oriented fibers, neurite extension perpendicular to the short fiber orientation is blocked and guided parallel to the oriented fiber direction. Analysis of the structure of the complete DRG demonstrates the orientation distribution of the growing axons (FIG. 19 C-D).

The Figures show:

FIG. 1: A liquid composite mixture, which consists of anisometric, magnetoceptive, soft microgels within a prepolymer surrounding (matrix) hydrogel, is injected at the injury, representing a minimal invasive approach. After injection the microgels are aligned within a magnetic field and the surrounding hydrogel crosslinks, fixing the microgel orientation and position. These function as barriers for ingrowing cells, directing their infiltration.

Figure 2:
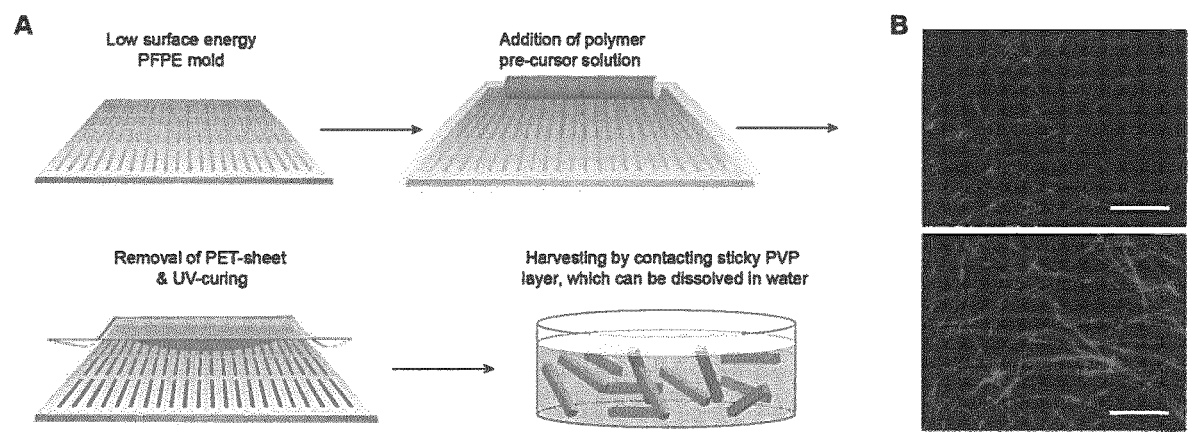

FIG. 2: Exemplary anisometric microgel fabrication via mold-based soft lithography. (A) Procedure of microgel fabrication: a low-surface energy polymer PFPE mold replica is cast with a polymer pre-cursor solution using a sacrificial PET-sheet. After removal of the sheet, the solution captured within the cavities is UV-crosslinked and harvested with a PVP layer. (B) Anisometric sPEG-A microgels with sizes of 5×5×50 µm (top) and 5×5×500 µm (bottom). All scale bars are 50 µm. Green color: fluorescein.

FIG. 3: To generate microheterogeneous, anisometric microgels with different mechanical properties, ranging from less than 100 to more than 5000 kPa, different sPEG-A contents are mixed with a non-reactive polymer component (here sPEG-OH 3 kDa). All scale bars are 50 µm. Green color: fluorescein.

FIG. 4: Comparison of a homogeneous microgel, prepared by diluting sPEG-A with water, and a microporous heterogeneous microgel, prepared by diluting sPEG-A with a non-reactive polymer component (here 0.2 kDa PEG-OH). The loss of microgel (hydrogel) transparency by introducing the non-reactive polymer component and subsequent extraction in water is due to its heterogeneous structure, consisting of water-filled pores/voids and connecting polymer walls. Scale bars are 2 mm for the microgel (hydrogel) overview and 5 µm for FESEM images.

FIG. 5: Cryo-FE-SEM images of microgel (hydrogel) cross-sections after 4 min sublimation time. sPEG-A contents of 10, 20, or 30% (w/V) are blended with different non-reactive PEG compounds, cured, washed to remove the non-reactive compound, and frozen in liquid ethane. Frozen microgel (hydrogel) are cut inside the FE-SEM pre-chamber to visualize cross-sections. The pore size reduces upon an increasing sPEG-A content. All scale bars are 5 µm.

Figure 6:
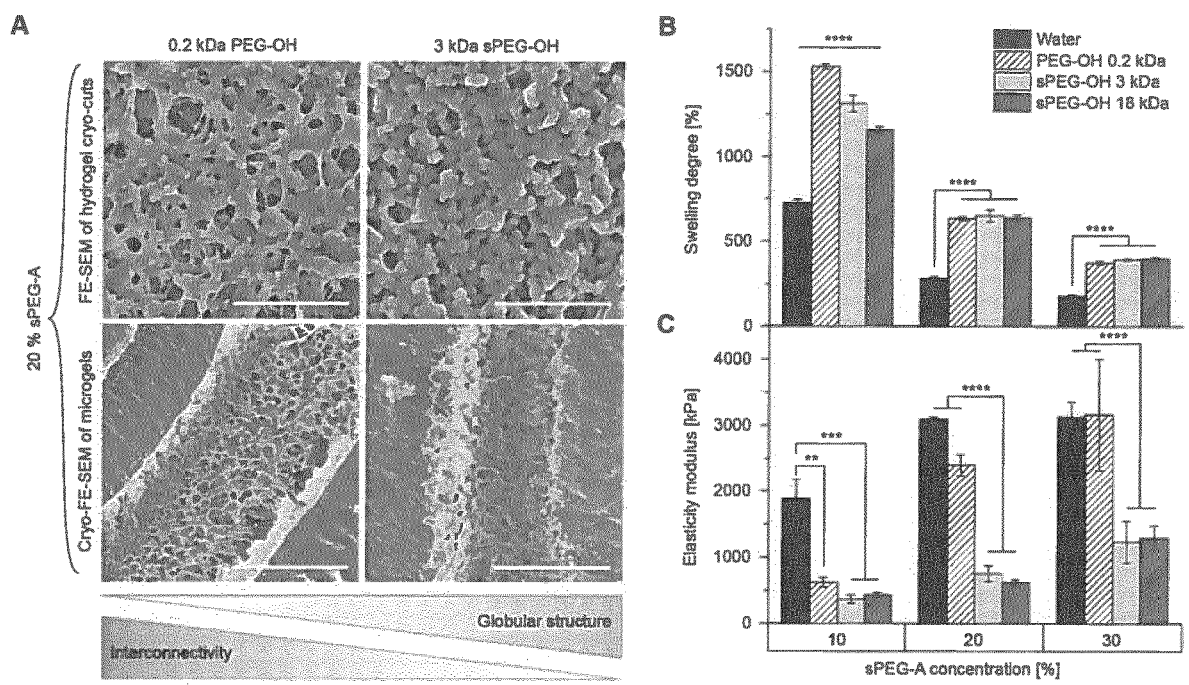

FIG. 6: Characteristics of microgel (hydrogel), fabricated with non-reactive PEG-OH compounds. (A) Microporous water-filled microgels. FE-SEM analysis of cryo-cuts of microgels (hydrogels) show a difference in the gel morphology. Microgels (hydrogels), prepared with low MW 0.2 kDa PEG-OH, show an interconnected structure in comparison to a more globular structure of microgels (hydrogels), fabricated high MW sPEG-OH (3 and 18 kDa). (B) The swelling degree of heterogeneous microgels (hydrogels) is significantly higher than homogeneous water-based microgels (hydrogels), which corresponds to the lower elasticity moduli in for almost all conditions (C). Data of both presented as average±s.d. and statistical significance performed using two-way ANOVA with Bonferroni comparison (p<0.01; *p<0.001; ****p<0.0001).

Figure 7:
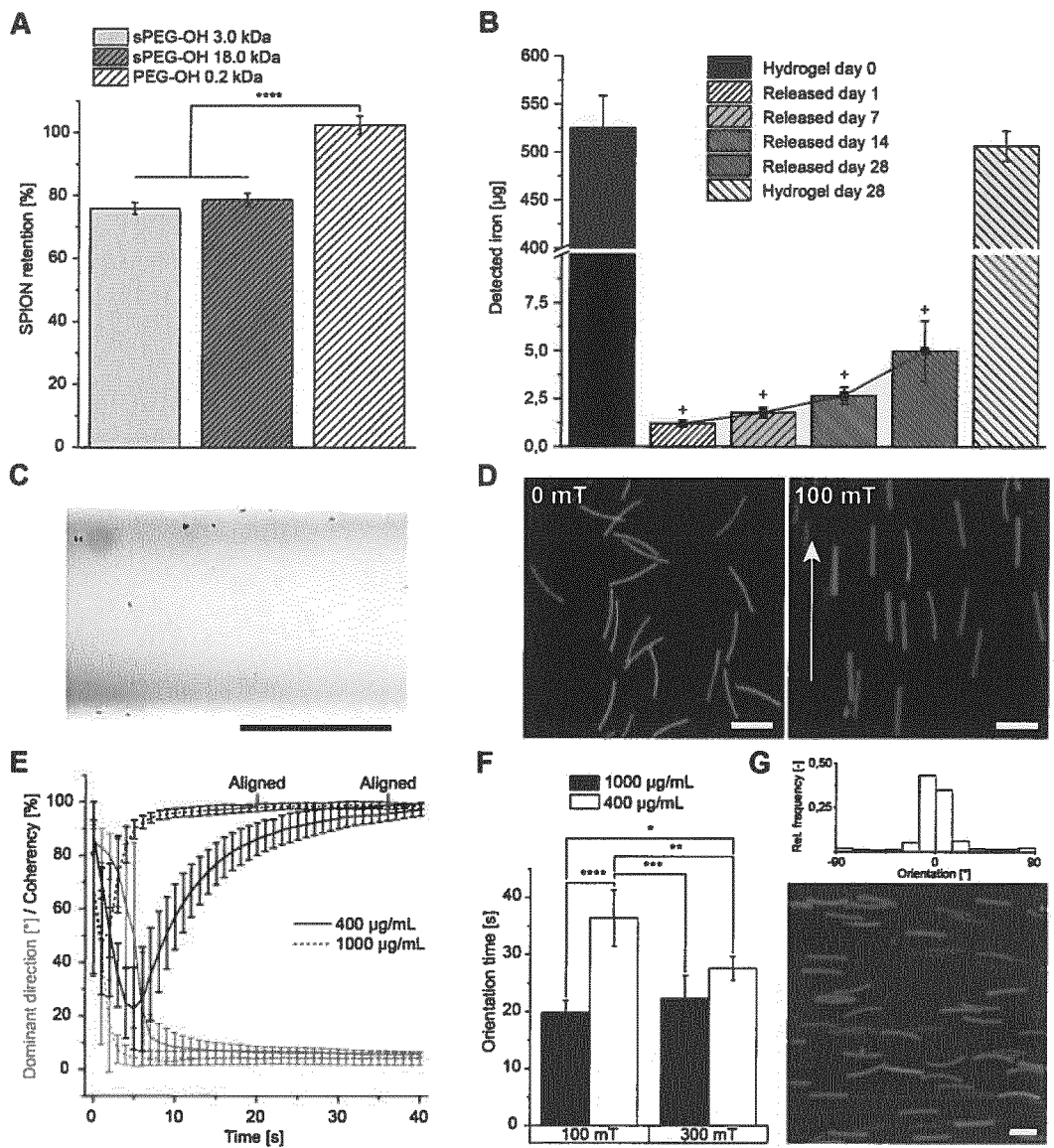

FIG. 7: Characterization of magnetoceptive microgels and hydrogels. (A) Retained SPIONs in 20% sPEG-A hydrogels, fabricated with different non-reactive compounds, after washing out the non-reactive compound. The highest retention capacity is observed for PEG-OH 0.2 kDa based gels. (B) Released iron amount over time, including amounts after washing at day 0 and after 28 days (+ means below sensitive region of device). (C) TEM of 1×1×10 µm microgel, loaded with 400 µg/mL SPIONs. (D) Incorporation of 400 µg/mL randomly distributed SPIONs inside the microgels resulted in microgel alignment in a 100 mT magnetic field. (E) The dominant direction and relative coherency (coherency to maximum coherency ratio) over a timespan of 40 s in a 100 mT magnetic field, determined by OrientationJ. When the relative coherency changes less than 0.1% per second over a period of 5 s, microgels are considered as aligned (see red marks), which is applied to determine the orientation times (F). (G) Fixation of magnetically aligned microgels in a surrounding fibrin gel and the distribution histogram by OrientationJ (Fourier gradient). Scale bars in D and G are 50 µm, in C it is 1 µm. Green: fluorescein; Red: Rhodamine-labeled fibrinogen. Data presented as average±s.d. and statistical significance performed using two-way ANOVA with Bonferroni comparison (*p<0.05; p<0.01; *p<0.001; ****p<0.0001).

Figure 8:
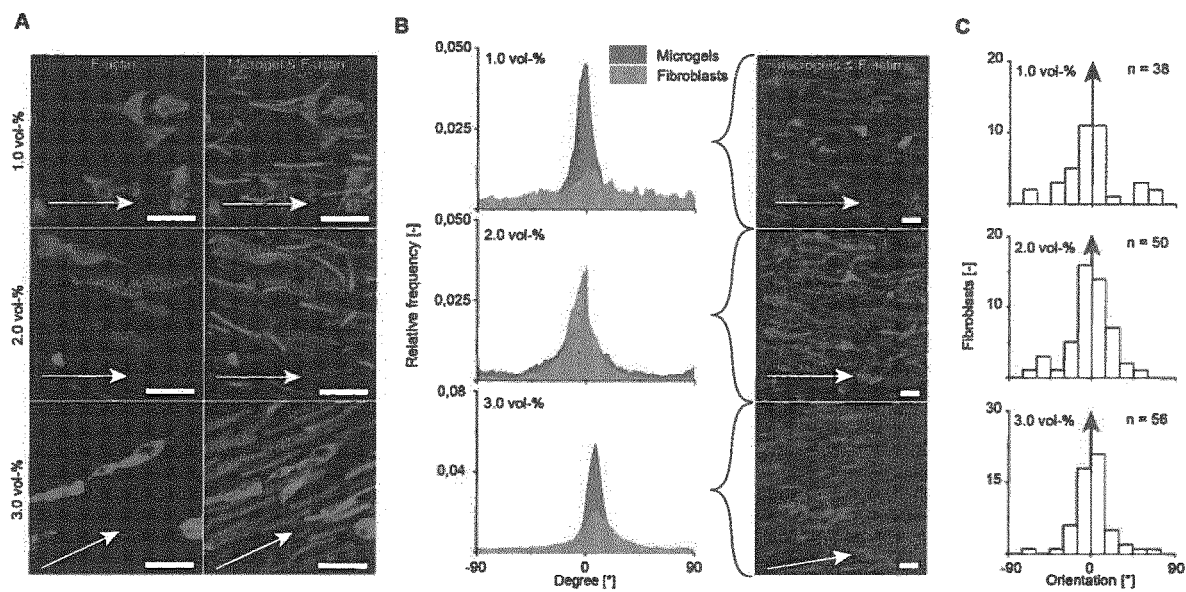

FIG. 8: Ability of the composite hydrogel matrix to align cell growth. (A) Fibrin hydrogels are doped with different concentrations of microgels (1.0, 2.0, and 3.0 v %), which are aligned in a magnetic field of 130 mT. Pre-mixed fibroblasts extend along the longitudinal microgel axis (green: fluorescein), visible by the stretched F-actin filaments (red: Alexa Fluor 594 phalloidin), depending on the microgel concentration. (B) Distribution of microgel and fibroblast (F-actin) orientation of 1.0, 2.0, and 3.0 v % microgels in low magnification images, showing cell orientation in the direction of the magnetic microgel orientation for 2.0, and 3.0 v % microgel concentration, but not for 1.0 v %. (C) Quantification of single fibroblast orientation in composite with different microgel concentrations in relation to microgel orientation (green arrow). 3D confocal images from different gels are analyzed with n equal to the number of analyzed cells. Scale bars are 20 µm.

FIG. 9: Neurite outgrowth of DRG in a fibrin gel without microgels (β-tubulin staining red: FITC).

Figure 10:
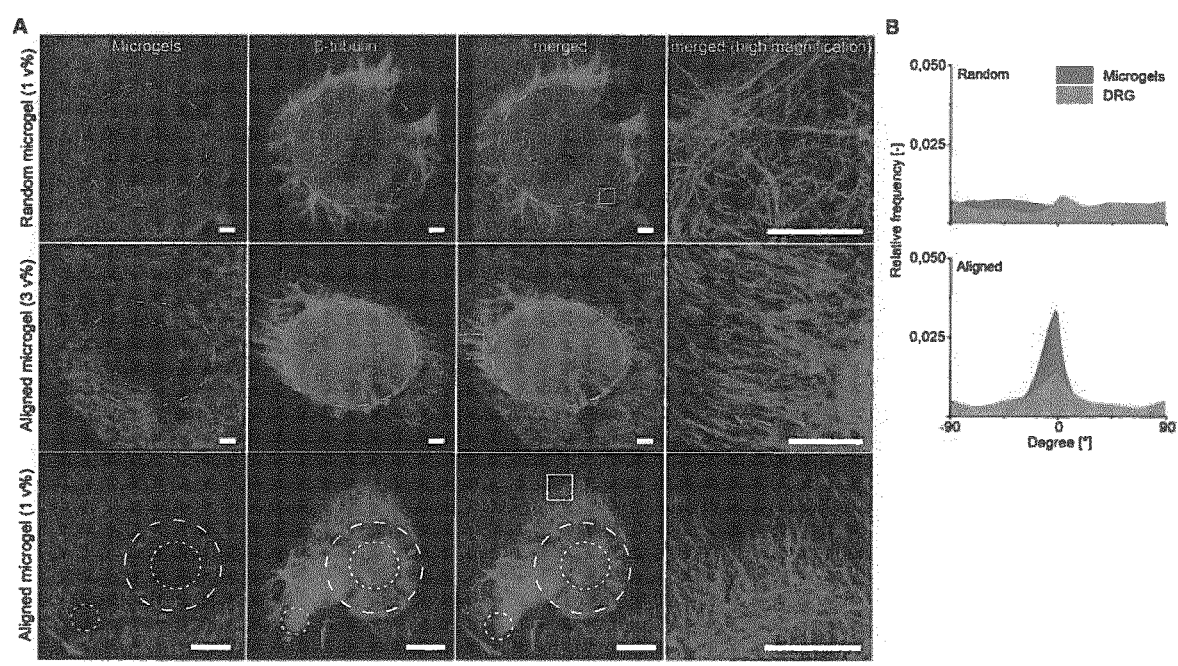

FIG. 10: Ability of the composite hydrogel matrix to align cell growth. (A) DRG-growth in aligned and random microgel-in-fibrin composites. β-tubulin staining (red: FITC) reveals neurite outgrowth along the microgel orientation for aligned microgels after an initial outgrowth burst in all directions. Inner circle marks inserted DRG, outer dotted circle shows the region of non-oriented microgels adjacent to the DRG resulting in an initial, randomly oriented growth burst; box marks high magnification region. (B) Distribution of DRG and microgel orientation from low magnification images in D. Scale bars are 200 µm.

Figure 11:
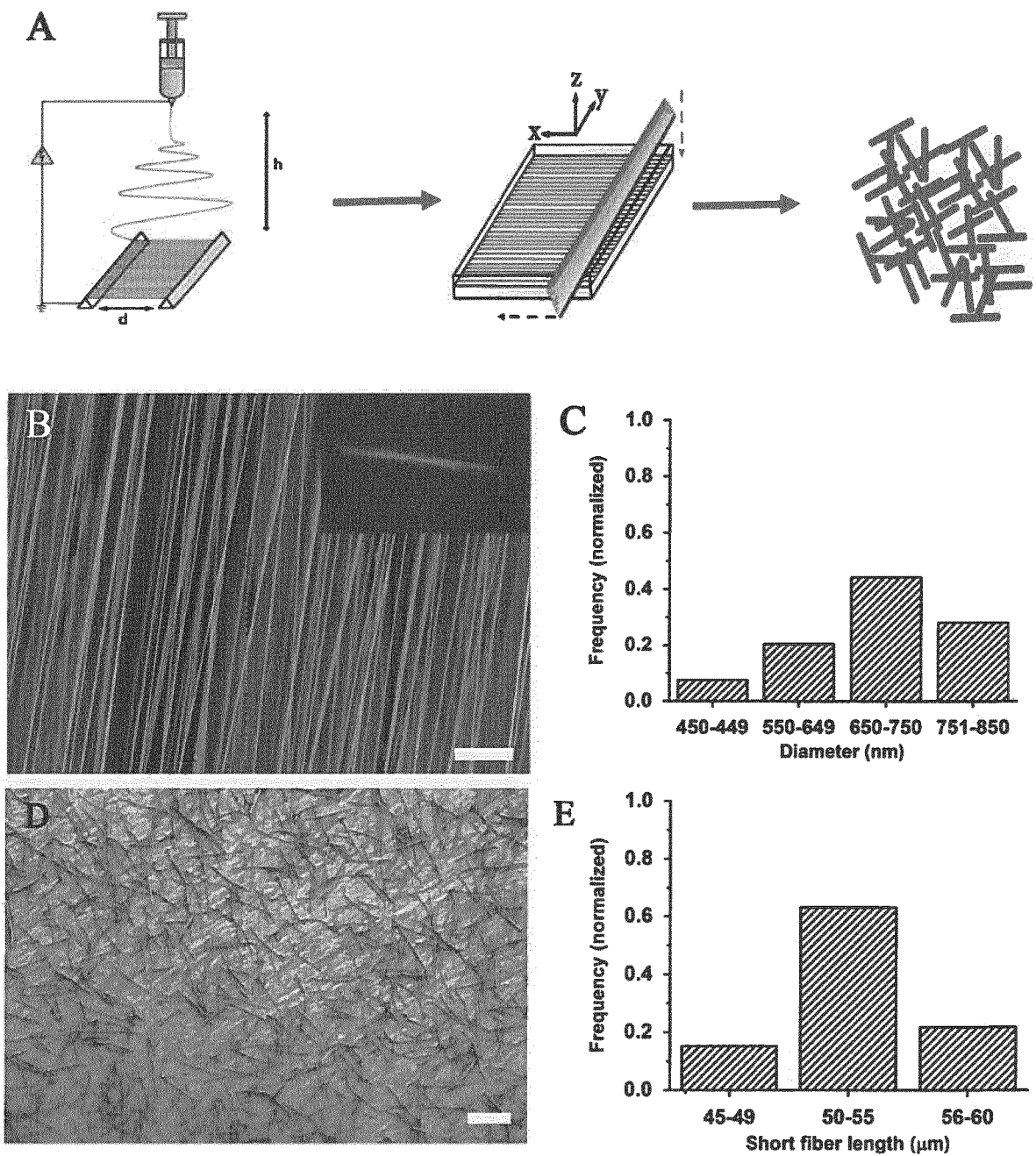

FIG. 11: (A) Schematic image of the short fiber production (electrospinning/cryosectioning) process. (B) SEM image of aligned PLGA fibers, with an average diameter of 690±88 nm collected on parallel plate. The inset image represents the 2-D fast fourier transformation (FFT) alignment analysis of the fibers (C) Fiber diameter distribution histogram. (D) Short uniform fibers produced by cryosectioning. (E) Short fiber length distribution histogram. Scale bars are 50 µm.

Figure 12:
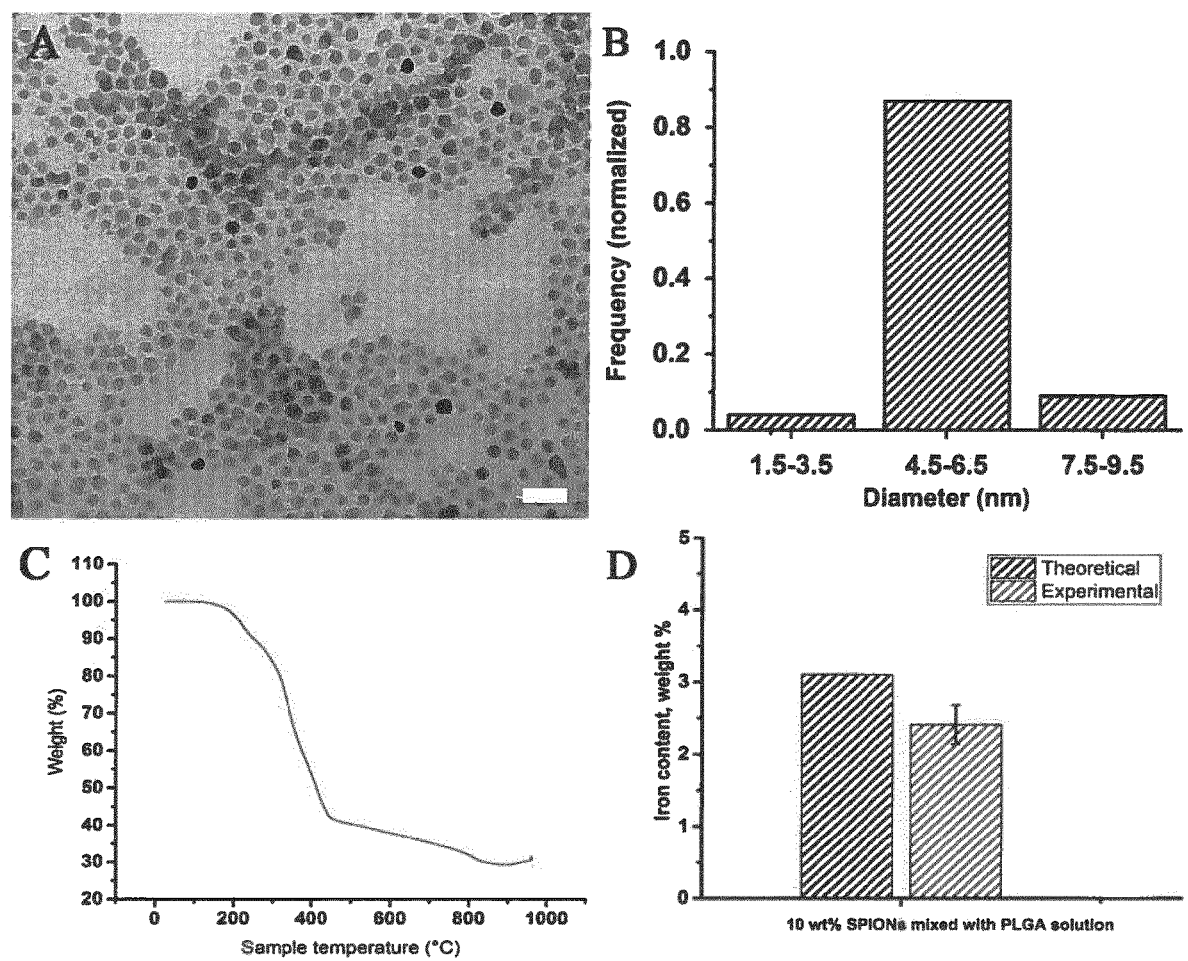

FIG. 12: (A) TEM image of synthesized SPIONs (scale bar 20 nm). (B) Size distribution of synthesized SPIONs. (C) TGA graph of dried SPIONs. (D) Iron oxide encapsulation efficiency into PLGA fibers.

FIG. 13: Orientation time of short magnetic fibers. The orientation time is decreased for higher magnetic fields, higher SPION concentrations, and shorter fiber lengths.

FIG. 14: Z-depth coded laser scanning confocal microscope of short magnetic PLGA fibers, fixed within a fibrin gel: (A) in the absence of a magnetic field, (B) after orienting and removal of the magnetic field (scale bar 100 µm). Orientation distribution of short magnetic PLGA fibers, fixed within a fibrin gel: (C) in the absence of a magnetic field, (D) after orienting fibers and removal of the magnetic field.

FIG. 15: (A) Random fibroblast growth inside an isotropic hydrogel without fibers. (B) Aligned fibroblast growth in the direction of short oriented PLGA fibers (indicated by arrow) inside an anisotropic hydrogel. (C-D) Orientation distribution of fibroblasts growth in (C) hydrogel without fibers and (D) in hydrogel with oriented short fibers Scale bars are 50 µm.

FIG. 16: SEM image of PCL fibers with different surface topographies: (A) Smooth fiber using chloroform-DMF (50:50, v:v) as the solvent system. (B) Grooved fiber using chloroform-DMF (90:10, v:v) as the solvent system. (C) Porous fiber using chloroform-acetone (75:25, v:v) as the solvent system. Scale bars are 5 µm.

Figure 17:
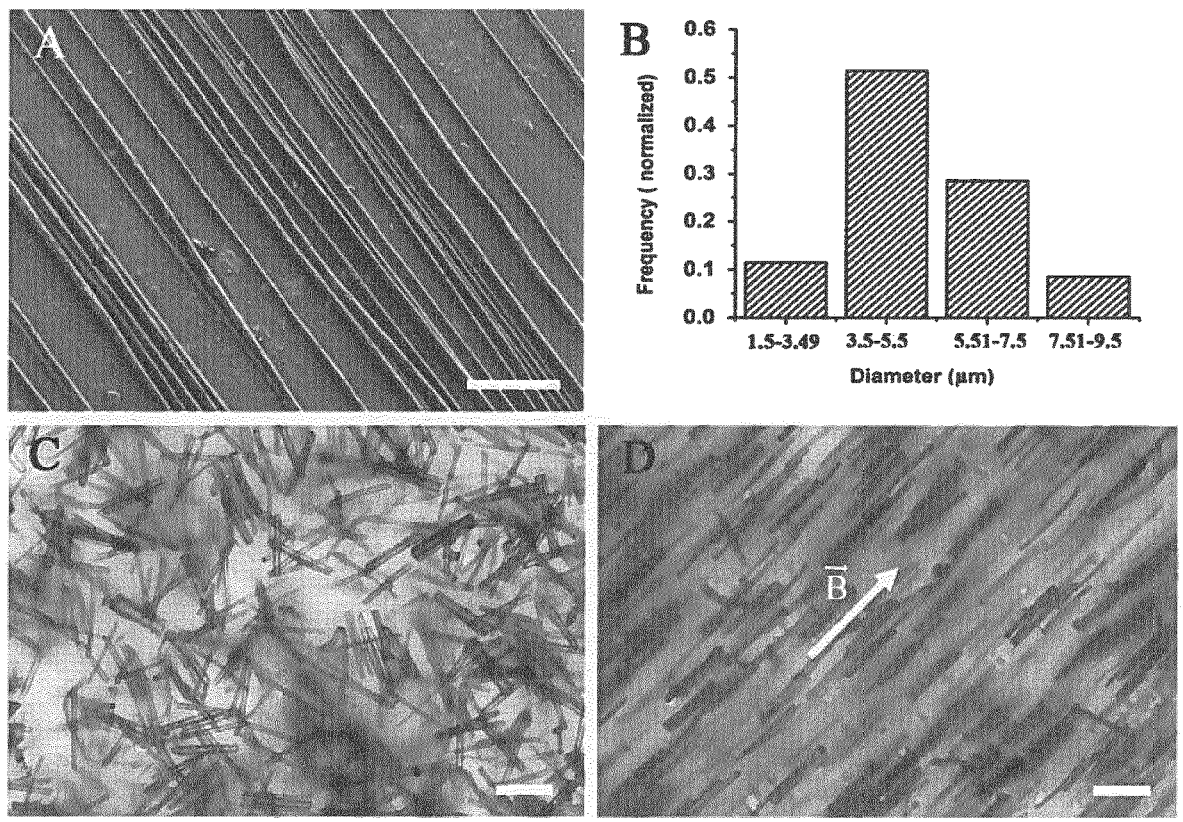

FIG. 17: (A) SEM image of aligned PCL electrospun fibers, with an average diameter of 5.3±1.4 µm collected on rotating drum (B) Fiber diameter distribution histogram graph. (C-D) Short magnetic PCL fibers, fixed within a fibrin gel: (C) in the absence of a magnetic field, and (D) after orienting and removal of the magnetic field (scale bar 100 µm).

FIG. 18: (A) Random fibroblast growth inside an isotropic hydrogel without short fibers. (B) Aligned fibroblast growth in the direction of short oriented PCL fibers (indicated by arrow) inside an anisotropic hydrogel. (C-D) Orientation distribution of fibroblast growth in (C) hydrogel without short fibers and (D) hydrogel with oriented short fibers (scale bars are 50 µm).

FIG. 19: (A-B) Neurite outgrowth of DRG in a fibrin gel with (A) randomly oriented PLGA short fibers and (B) oriented PLGA short fibers. (C-D) Orientation distribution of DRG extensions in (C) hydrogel with randomly oriented short fibers and (D) hydrogel with oriented short fibers (scale bars are 500 µm).

The invention is described in more detail in, but not limited to, the following examples.

EXAMPLES

1. Anisometric Microgels as Anisometric Elements

Synthesis and Analysis of 3 kDa 6-Arm Star PEG-Acrylate

The functionalization of 6-arm poly(ethylene oxide-stat-propylene oxide) (6-Arm star-PEG, consisting of 80% ethylene oxide and 20% propylene oxide (sP(EO-stat-PO)) provided by CHT R. Beitlich GmbH) with acrylate groups (sPEG-A), is performed according to M. C. Lensen et al., Micro- and Nanopatterned Star Poly(ethylene glycol) (PEG) Materials Prepared by UV-Based Imprint Lithography. *Langmuir* 23, 7841-7846 (2007). In short, hydroxyl-terminated sP(EO-stat-PO) (3 kDa) (101.80 g, 0.204 mol OH groups) is dried at 80° C. for 20 h. Subsequently, toluene (750 mL) and pyridine (24.2 g, 0.306 mol, 1.5 eq) are added to the solution. Acrylic acid anhydride (33.38 g, 0.265 mol, 1.3 eq) is added dropwise to the solution at room temperature. After stirring for 24 h, toluene is removed under reduced pressure and the residue is taken up in dichlormethane, and the polymer purified by precipitation cold diethyl ether (5 times).

Degree of functionalization is determined by $^1$H NMR analysis with a Bruker DPX-400 FT NMR spectrometer (400 MHz). Results are reported as follows: chemical shift d (ppm) (multiplicity, number of protons, assignment). TMS ($\delta$=0.0 ppm) is used as internal standard. Chemical shifts are reported to the nearest 0.01 ppm. Yield: 72.3 g (64%). Degree of functionalization: 98%. $^1$H NMR (CDCl$_3$): $\delta$ (ppm)=1.08 (d, 3H, —CH$_3$ PEG), 1.20 (d, 3H, PEG-OCH$_2$CH(CH$_3$)OCOCHCH$_2$), 3.20-3.80 (m, PEG backbone), 4.20-4.30 (m, 2H, PEG-CH$_2$CH$_2$OCOCHCH$_2$), 4.94-5.16 (m, 1H, PEG-CH$_2$CH(CH$_3$)OCOCHCH$_2$), 5.74-5.84 and 6.27-6.42 (m, 2H, PEG-OCOCHCH$_2$), 6.00-6.12 (m, 1H, PEG-OCOCHCH$_2$).

Molecular weights (M$_n$ and M$_w$) and dispersity values (Đ=Mw/Mn) are determined by size exclusion chromatography (SEC) as M$_n$=2200 g/mol; M$_w$=2300 g/mol; Đ=1.1. SEC analysis is carried out with dimethylformamide (DMF, HPLC grade, VWR). DMF-SEC is performed using an Agilent 1100 system equipped with a dual RI-/Visco detector (ETA-2020, WGE). The eluent contains 1 g/L LiBr (≥99%, Sigma Aldrich). The sample solvent contains traces of water (HPLC grade, VWR) as internal standard. One pre-column (8×50 mm) and four PSS Gram gel columns (8×300 mm) are applied at a flow rate of 1.0 mL/min at 40° C. The diameter of the gel particles measured 10 µm, the nominal pore width were 30, 10$^2$, 10$^3$ and 3000 Å. Calibration is achieved using narrowly distributed PEG standards (PSS Mainz). Results are evaluated using the PSS WinGPC UniChrom software (version 8.1).

Preparation of Microgel Pre-Polymer Solution

10% (w/V) of the photoinitiator 2-Hydroxy-4'-(2-hydroxyethoxy)-2-methylpropiophenone (Irgacure 2959) is dissolved in DMSO and added to the required amount of sPEG-A in a molar ratio of 1% acrylates. 20 mg/mL fluorescein-o-acrylate was added for fluorescence tracking. For water-based solutions components are dissolved in 70% ethanol. After stirring for 4 h, a pre-polymer solution is used pure or diluted in non-reactive compound (200 g/mol PEG-OH, 3000 g/mol sPEG-OH, 18000 g/mol sPEG-OH) or water.

Fabrication of Microgels with Mold-Based Soft Lithography

Before usage, silica wafer are cleaned by 20 min incubation in acidic piranha solution (3:1 sulfuric acid to hydrogen peroxide), washing in water, and 10 min sonication in acetone and isopropanol. Mold-based soft lithography methodology is derived from K. P. Herlihy, J. Nunes, J. M. DeSimone, Electrically driven alignment and crystallization of unique anisotropic polymer particles. *Langmuir* 24, 8421-8426 (2008). In short, perfluoropolyether molds are prepared by pouring the pre-polymer with 1 w % Irgacure 1173 onto an inverse-patterned silica wafer and UV-curing for 120 min under a constant nitrogen stream. Via a supportive PET-sheet, molds are peeled off wafer. Microgel pre-polymer solution is cast onto mold and spread via a sacrificial PET-sheet. Upon removal of PET, molds are placed within a nitrogen atmosphere and UV-cured for 60 min. Excess gel is cut off and the mold is placed into a 50% (w/V) PVP layer and tightly pressed. The glue layer is dried for one week at 45° C., followed by removal of the mold. Microgels are dispersed in water and purified by centrifugation at 4500 g for 10 min and re-dispersion in water, which is repeated two times.

Preparation and Characterization of sPEG-A Hydrogel Disks

A PDMS layer of 1 mm thickness is punched to form 12 mm round cavities, into which the pre-polymer solution is casted. The cavity is enclosed by flat PDMS layers. The pre-polymer solution is gelled by UV-curing for 1 h in nitrogen atmosphere inside a glovebox (InerTec AG). Gel disks are washed three times in water for 30 min to remove the non-reactive compound and non-incorporated SPIONs. Swelling degrees are determined by weighing the hydrogel disks at room temperature in the water swollen state and after drying for 24 h at 40° C. For mechanical characterization, hydrogel disks are subjected to unconstrained compression at room temperature using a DMA device (Q800 DMA, TA Instruments) equipped with a submersion clamp. The elasticity modulus is calculated from the slope of the linear region of stress-strain curves, obtained by applying a force ramp of 1N/min towards the samples. For cryo-FE-SEM, swollen gels are frozen in liquid ethane for 1 min and transferred into liquid nitrogen. Hydrogel cross-sections are cut inside the FE-SEM pre-chamber and samples are visualized at 1 kV and 1 µA with FE-SEM SU4800 (Hitachi Ltd. Corporation) after 4 min sublimation (FIG. 5) down to −80° C. Microgel dispersions are loaded onto rivet sample holders and correspondingly frozen and visualized after 6 min sublimation. For cryo-sections, hydrogels are embedded in O.C.T. gel inside a 10×10×5 mm cryo molds and frozen in liquid nitrogen. A Cryotome (Leica Camera AG) is used to polish the sample and cut sections of 10 µm thickness, which are collected onto glass slides. For FE-SEM imaging, samples are sputtered with gold/palladium (Sputtercoater EM ACE600, Leica) before FE-SEM analysis with 5 kV and 5 µA.

Dispersion and Quantification of SPIONs

Before usage, SPIONs are ultrasonicated 5 min on ice with an amplitude of 10% and a treatment interval of 1 s to 1 s break. The non-reactive polymer compound is mixed with the desired amount of SPIONs in water, making up 5 v % of the dispersion, and ultrasonicated with the same parameters. sPEG-A with photoinitiator and fluorescein-o-acrylate is blended and ultrasonicated for 1 min. The final dispersion is stored on ice and was used for molding within 30 min. For quantification of SPION retention, a relatively high amount of SPIONs (5.44 mg/mL) is dispersed in the pre-polymer solutions to achieve detectability. Gels of 25 µL volume are cured for 120 min with UV in nitrogen atmosphere and afterwards washed for at least 3 times 30 min in water. These are dried at 40° C. for 48 h and ionized for elemental analysis via first nitric acid (65%) treatment and second hydrochloric acid (30%) in microwave. The ICP-atom emission spectrometer Plasma 400 (Perkin Elmer) is used for iron quantification with a reliable quantification limit of 50 µg/L. For the release studies, SPION-loaded hydrogels are incubated in 1 mL PBS for 1, 7, 14, and 28 days at 37° C., and supernatant is replaced by fresh PBS for every measurement interval. TEM measurement of microgels are performed by molding 400 µg/mL SPION, sPEG-A, and PEG-OH 0.2 kDa pre-polymer blend into 1×1×10 µm mold features. After curing and harvesting microgels are purified as above and placed onto carbon-coated cupper grids (PLANO, CF300-CU). Microgels are dried for 24 h at 40° C. and visualized by the STEM SU9000 (Hitachi Ltd. Corporation) in TEM mode at 30 kV.

Analysis of Microgel Orientation

For orientation analysis, purified microgels (see above) are counted with a Neubauer counting chamber and the concentration was adjusted to $5*10^5$ microgels/mL. Aliquots of 10 µL are pipetted onto small glass pieces, which are placed in magnetic inserts of 100 or 300 mT magnetic fields (LUM GmbH). To determine the longest possible orientation time, microgels are pre-aligned, followed by a shift of the magnetic field of 90°. The orientation rotation is recorded by bright field microscopy time-lapse experiments with 1 image/s. The videos are imported into ImageJ and the dominant orientation and coherency are measured with the plugin OrientationJ. As the dominant orientation is quickly reached, despite an ongoing alignment enhancement, the stagnation of the relative coherency is applied for determination of the orientation time. When the relative coherency (related to maximum coherency) changes less than 0.1% per second within an interval of 5 s, the 5th point (second 5) is considered as the moment of alignment and determined as the orientation time (see red marks in FIG. 7E).

To fix the microgel position and orientation, the microgels are mixed with fibrinogen (4 mg/mL). After 15 min activation at 37° C. of the enzyme solution, consisting of factor XIII (fibrogrammin, 4 U/mL), thrombin (0.125 U/mL), and calcium chloride in HEPES buffer (5 mM), both components are mixed and microgels are aligned in magnetic inserts for 20 min at 37° C. To label the fibrin, 20 µg/mL of the applied fibrinogen is labeled with the NHS-Rhodamine Antibody Labeling Kit (Thermo Scientific) according to the manufacturer's protocol. Images are acquired by laser scanning confocal microscopy and relative distribution of orientation is determined by OrientationJ (Distribution function, Fourier Gradient, Gaussian window 1 pix, 70% minimum coherency, 2% minimum energy according to R. Rezakhaniha et al., (Experimental investigation of collagen waviness and orientation in the arterial adventitia using confocal laser scanning microscopy. *Biomech Model Mechanobiol* 11, 461-473 (2012)) with 15° binning.

Cell Culture

Cell culture experiments are carried out with L929 mouse-derived fibroblasts or isolated dorsal root ganglia (DRGs) from day 10 chicken embryos. Fibroblasts are cultured in a basal medium consisting DMEM, supplemented with 10% fetal bovine serum and 1% antibiotics/antimycotics, at 37° C., 5% $CO_2$ and 95% humidity. Microgels (see above) require extensive washing steps to be applicable for cell experiments, consisting of acetone washing for 2 h before harvesting and 2× ethanol, 2× water, 2× medium after harvesting.

For MTS cell viability analysis, equivalently washed hydrogels with SPIONs are incubated 24 h in medium, which is sequentially applied onto cells (5000 cells/well in 96 well plate) after one day cultivation. At day 0, 2, and 5, medium/extracts are refreshed and 20 µL MTS reagent is added to the respective measurement wells. MTS signals after 3 h are used for survival and proliferation rate determination.

To assure sterility while applying a magnetic field for composite hydrogels, glass bottom PDMS wells are prepared (5 mm inner diameter, 8 mm outer diameter) by treating upper surfaces of PDMS and glass with oxygen plasma for 10 s with 250 W (41 mL/min oxygen flow) and attaching PDMS and glass covalently. These are autoclaved before cell experiments. Magnetic inserts are built by separating two cylindrical magnets (10 mm diameter, 3 mm thickness, N42) with stainless steel. The magnets are glued with the insert by 2K metal glue and disinfected by 70% ethanol and 30 min UV irradiation prior to use.

For orientation of microgels with fibroblasts, washed microgels are counted with a Neubauer chamber and the concentration was adjusted accordingly (volume per microgel corresponded to PFPE mold cavity volume). Microgels in media are mixed with fibrinogen (8 mg/mL) and the activated enzyme solution (same conditions as described above) and 30 µL of the liquid solution is inserted per PDMS well, which is standing in the middle of the magnetic insert. The filled wells are kept for 10 min inside the inserts, followed by 10 min at 37° C. inside a 24 well plate to assure complete gelation without the presence of a magnetic field. Afterwards, 1.5 mL of basal medium is added, consisting of RPMI, supplemented with 10% fetal bovine serum and 1% antibiotics/antimycotics and fibroblasts are cultivated for 2 days at 37° C., 5% $CO_2$ and 95% humidity.

For orientation of microgels with dorsal root ganglia (DRGs), fertilized chicken eggs from top-class brown laying hens (bruteiershop.de) are incubated for 10 days at 37° C. and a humidity of 40-50%. DRGs are isolated and stored in Hank's Balanced Salt Solution (HBSS), supplemented with 6 g/L glucose until use. For cultivation of DRGs in composite hydrogels, the composite pre-cursor solution is prepared (4 mg/mL fibrinogen; enzyme solution as before), and pipetted into a glass-bottom PDMS well. DRGs are then placed in the middle of the non-crosslinked microgel-fibrin composites with a Ti #5 forceps, while being positioned in the magnetic insert. After 10 min, gels are transferred into a 24 well plate and incubated for 10 min at 37° C. When gelled, 1.5 mL of DMEM medium is added, supplemented with 10% fetal bovine serum, 1 antibiotics/antimycotics, and 10 ng/mL NGF. DRGs are cultivated at 37° C., 5% $CO_2$ and 95% humidity for 5 days and after 2 days media is exchanged.

Staining of Cells

Cells are first washed 30 min with 1×PBS and fixed with 4% paraformaldehyde for 60 min, followed by 2 times washing with PBS for 30 min. 0.1% Triton-X 100 was added and incubated for 60 min. Samples are washed 2 times with PBS again for 30 min and then blocked for 60 min with 1% BSA. Afterwards, primary antibodies are added (1:1000 Alexa Fluor 594 Phalloidin for the fibroblasts, 1:250 Tuj1 monoclonal antibody mouse-derived for the nerve cells), and incubated overnight, followed by 3 times washing for 30 min with PBS. In case of neuronal staining, a secondary antibody (1:100 Rhodamine (TRITC) goat-derived anti mouse antibody) is added, incubated for 4 h and washed 3 times with PBS. In case of nucleus staining, DAPI is added, incubated for 1 h and washed 3 times with PBS for 30 min. Samples are visualized with laser scanning confocal microscopy, using a photodiode 405 (DAPI), argon laser adjusted to 488 nm emission (fluorescein in microgels), or diode pumped solid state laser 561 nm (Phalloidin, Rhodamine).

Analysis of Cell Orientation

For distribution of orientation, OrientationJ Distribution function is applied, using the Fourier Gradient, a Gaussian window of 1 pix, and a minimum coherency of 20% and a minimum energy of 2% (fibroblasts) or 5% (DRGs). Counts per degree are related to the sum of all counts, giving the relative frequency. Single cell analysis is performed with the OrientationJ Measure function, where randomly selected single cells are marked and their orientation is determined. Coherencies below 20% are filtered out to assure high enough quality of the determined orientation. Afterwards, cell orientation is related to the microgel orientation (FIG. 6C).

Statistical Analysis

Statistical analysis is performed with OriginPro 2016G. Depending on the number of groups a one-way (FIG. 3A) or two-way (FIG. 2D, E, 3F) ANOVA is executed with post-hoc Bonferroni comparison for evaluation of statistical significance between groups (*p<0.05, p<0.01, *p<0.001, ****p<0.0001). Data shown as mean average with error bars indicating the standard deviation.

Electrospun Fibers with SPION Incorporation

SPIONs synthesis: SPIONs are prepared as described in Wang C Y, Hong J M, Chen G, Zhang Y, Gu N. Facile method to synthesize oleic acid-capped magnetite nanoparticles. Chinese Chemical Letters. 2010; 21:179-82.

Briefly, first 10 mL aqueous solution containing 6 mmol ammonium iron(II) sulfate hexahydrate $(NH_4)_2Fe(SO_4)_2 \cdot 6H_2O$ (Sigma-Aldrich, Germany) is added into a 100 mL three-necked round bottom flask with nitrogen to remove oxygen, followed by the addition of 10 mL oleic acid vegetable (VWR, Germany), 10 mL 25% (w/w) tetramethylammonium hydroxide solution $(CH_3)_4N(OH)$ (Sigma-Aldrich, Germany), and 35 mL DMSO (Sigma-Aldrich, Germany) as main solvent as well as oxidant of the reaction system. The mixture is stirred and refluxed at 140° C. for 1 h while the color gradually changes from brown to black. After removing the flask from the oil bath and letting it to be cooled to room temperature, superparamagnetic iron oxide nanoparticles precipitates are obtained and washed with excess of ethanol (Sigma-Aldrich, Germany) by magnetic separation. Subsequently, the final precipitate is re-dispersed in chloroform (Sigma-Aldrich, Germany).

Electrospinning: PLGA (75:25, RESOMER® RG 756 S, Evonik Industries) with the concentration of 18 w/v % is dissolved in 90:10 v/v chloroform: DMF (Sigma-Aldrich, Germany) under gentle stirring for 1 h to obtain a homogeneous solution. Different amounts of synthesized SPIONs (1, 5 and 10 of polymer wt %) are distributed into the polymer solution with 10 min ultrasonication prior to the electrospinning process.

PLGA polymer solution containing SPIONs is pumped through a 21G needle, which is connected to the cathode of a DC voltage source. A grounded parallel plate assembly is used as counter electrode to collect the aligned fibers. The flow rate is fixed at 0.5 $mLh^{-1}$, and voltage is varied in the range of 7-8.5 kV.

PCL (75 kD, Sigma-Aldrich, Germany) is dissolved in different solvent systems in order to obtain solutions with 13 wt %, 15 wt %, and 17 wt % concentration. Smooth fibers are collected on a low speed rotation drum (50 rpm) with 15 wt % solution in chloroform:DMF (50:50, v/v) solvent mixture. In order to get fibers with a groove surface morphology, 17 wt % solution is prepared in Chloroform:DMF (90:10, v/v). Porous fibers result from changing the solvent system to chloroform:acetone (75:25, v/v). Solutions with a 13 wt % PCL concentration lead to fibers with an average diameter of 2.01±0.95 μm while higher concentrations result in larger diameters up to 15 μm.

Iron Oxide Encapsulation Efficiency:

In order to evaluate the real amount of encapsulated iron oxide in the electrospun fibers, thermal gravimetric analysis (TGA) was done for a dried SPION solution, fibers with and without SPIONs. TGA analysis of the dried SPION solution showed 31 wt % iron oxide with the other 69% being oleic acid, residual organic solvent and probably water, which were all burned during the temperature increase from 30° C. to 1000° C. (FIG. 12C). Considering that 31 wt % of SPION solution is actually iron oxide, the theoretical amount of iron oxide in the PLGA fibers containing 10 wt % ION was calculated and compared with the experimental value of iron oxide resulting from TGA analysis of the same fibers (FIG. 12D). This comparison suggests a 78% encapsulation efficiency of iron oxide after electrospinning.

Cryosectioning:

Aligned nano/micro fibers are harvested from the collector and placed in a rectangular custom designed polyethylene cryomold. Optimal cutting temperature (OCT) gel (Sakura Finetec) is added and the mold was frozen in liquid nitrogen, resulting in a rectangular block of solidified gel with the aligned fiber stack embedded therein. The frozen block is sectioned using a cryostat microtome maintained at −20° C. Harvested sections are allowed to warm up to room temperature followed by dissolving and removing the OCT gel by washing repeatedly with deionized water.

Preparation of hydrogel with short fibers: custom designed single wells with glass bottom are fabricated with PDMS. Isotropic distribution of short fibers is achieved by gelation of the fibrinogen gel without applying an external magnetic field. To fabricate an anisotropic matrix, the small PDMS well is placed in the 1 cm gap of a cuvette magnet (LUMiSizer) with magnetic field intensities of 100, 200 and 300 mT.

After production and purification of the anisometric elements via PRINT or electrospinning, the experimental methods to culture, stain, and analyze the cells are similar.

Conclusion

The present invention relates to a novel hierarchically-designed material class for the regeneration of soft sensitive tissues, which require injection and the formation of anisotropic structures. By applying magnetoceptive, anisometrically alignable soft anisometric microgels as building blocks to create a unidirectional structure, high control can be obtained of numerous parameters, such as chemistry, dimension, shape, stiffness, porosity, permeability and water content. This enables specific modifications to tailor the macro- and microenvironment according to the cell's demands. The anisometric elements are rendered magnetic by mixing a low concentration of magnetic particles, particularly SPIONs, inside their structure to reduce iron toxicity. In the course of the present invention, it has been demonstrated that, for example, fibroblasts and nerve cells respond to the anisotropic structure by growing linearly along the anisometric elements' longitudinal axis. This composite represents a novel and versatile tissue regenerative material, which fills a gap between the existing biomaterial constructs that require implantation and injectable isotropic materials. It is the first biomaterial that can achieve highly controlled and ordered structures in situ after injection to guide tissue repair with the correct architecture. This feature is crucial to regain tissue functionality that depends on its structural organization, and can be very useful as supporting therapeutic material for e.g. spinal cord repair.

The invention claimed is:

1. A macroscopically alignable, injectable, soft hydrogel composition comprising:
   (a) longitudinally alignable, anisometric magnetoceptive microgel elements having a Young's modulus in the range of 10 kPa-50 MPa, and having an aspect ratio of 1.5 or higher, and comprising magnetic particles distributed within, and
   (b) a crosslinkable biocompatible matrix hydrogel composition comprising said anisometric elements, wherein the anisometric elements are distributed within the matrix hydrogel composition,
   wherein the hydrogel composition is injectable and wherein the longitudinal alignment of the anisometric elements and crosslinking of the matrix hydrogel occur in situ, and wherein the microgel elements are present in the injectable hydrogel composition in an amount of 0.1 to 10 vol.-%.

2. The hydrogel composition according to claim 1, wherein the magnetic particles have a mean particle size in the range of 1 to 50 nm.

3. The hydrogel composition according to claim 1, wherein the microgel elements have a diameter of 0.3-20 μm and a length 0.5-200 μm.

4. The hydrogel composition according to claim 3, wherein the diameter of the microgel elements is in the range of 1-5 μm and the length is in the range of 10-120 μm.

5. The hydrogel composition according to claim 1, wherein the matrix hydrogel/microgel material is selected from molecules, which are at least partly soluble in aqueous solutions, and can be derived from:

(i) natural components, which include fibrinogen, collagens, cellulose, Matrigel, (self-) assembling peptides or proteins, ribonucleic acids, desoxynucleic acid, albumins, antibodies and fragments thereof, blood plasma protein, gelatin, alginates, elastin, fascin, keratins, polyaspartate, polyglutamate, prolam ins, transferrins, cytochromes, flavoprotein, glycoproteins, hemoproteins, lipoproteins, metalloproteins, phytochromes, phosphoproteins, opsins, agar, agarose, arabinans, arabinogalactans, carrageenan, chitin, cellulose, carbomethyl cellulose, hydroxypropyl methylcellulose and other carbohydrate-based polymers, chitosan, dextran, dextrin, gelatin, hyaluronic acid and derivatives, mannan, pectins, rhamnogalacturonans, starch, hydroxyalkyl starch, xylan, (ii) synthetic components, which can be in linear, branched, dendrimeric, circular, or star shape or a combination of thereof, and which include the group of polyvinyl-based polymers, selected from poly(vinyl acetate), poly(vinyl alcohol), poly(vinyl acetale), poly (vinyl ether), poly(vinyl pyrrolidone), poly(vinyl amines), and poly(vinyl methylether), the group of poly (meth)acrylates, selected from polyacrylic acid, polyacrolein, polyacrylnitril, poly(cyanoacrylate), poly (acrylamide), poly (N-isopropyl acrylamide), poly(dimethylacrylamide), poly(hydroxypropyl-methacrylamide), poly(methylmethacrylate), poly(methacrylate), and poly(hydroxyethyl acrylate), the group of poly (oxymethylene)s, the group of polyethers, selected from poly(ethylene oxide), poly(propylene oxide), poly (tetramethyl oxide), poly(phenylene oxide), poly(ethylene glycol), poly(propylene glycol), and poly (vinyl methyl ether), the group of polycarbonates, selected from poly(trimethylene carbonate), poly(orthocarbonate), and poly(iminocarbonates), the group of polyesters, selected from poly(3-hydroxybutyrate), poly(glycolic acid), poly(maleic acid), polydioxanones, poly (propylene fumarate), poly(anhydrides), the group of polyamides, selected from poly(imino carbonates), poly(amino acids), and poly(aspartamide), the group of carbon/sulfur based polymers, the group of silicones selected from polysiloxane, and polydimethylsiloxane, the group of polyurethanes, the group of polyimides, selected from poly(succinimide), poly(bis-maleine imide), poly(oxa-diazo-benzimidazole), poly(imide sulfone), and poly(methacryl imide), the group of phosphorous based polymers selected from phosphoesters (polyphosphates, polyphosphonates), and polyphosphazenes (poly[di(carboxylatophenoxy)phosphazene], poly[di(methoxyethoxyethoxy) phosphazene]), the group of polyoxazoline, selected from poly(2-alkyl-2-oxazolines), poly(hydroxypropyloxazoline), and poly (hydroxyethyloxazoline), and any polyelectrolyte of the aforementioned polymers;

(iii) co-polymers, which can be alternating, statistical, periodic, or block or a combination of thereof, and which consist of the aforementioned aqueous-soluble polymers conjugated to another aqueous-soluble polymer or water-insoluble monomers, pre-polymers, or polymers, which include poly(c-caprolactam), poly (caprolactone), poly(lactic acid), poly(glycolic acid), poly(ethylene succinate), poly(butylene succinate), polyvinylchloride, polybutadiene, polyisoprene, polychloroprene, poly(ethylene terephthalate), poly(phenyleneterephthalamide), poly(ether sulfone), as for instance co-polymers, selected from poly(3-hydroxybutyrate-co-hydroxyvalerate), poly(butylene adipate-co-terephthalate), poly(butylene succinate-co-terephthalate), poly(ethylene-co-vinyl alcohol), poly (ethylene-co-acrylic acid), poly(ethylene-co-maleic acid), poly(ethylene oxide)-co-poly(propylene oxide) block copolymers, polyether imide, poly amid imide, divinyl ether-maleic anhydride (pyran) copolymer, N-(2-Hydroxypropyl) methacrylamide (HPMA) copolymers, polyacrylic acid copolymers, polylactic-co-glycolic acid, polyethylene oxide-co-polypropylene oxide, co-polyethylene oxide block or random copolymers, copolymers of poly(hydroxy acid)s, poly(orthocarbonate)s, poly(anhydride)s, poly(lactone)s, poly (aminoacid)s, poly(carbonate)s, and poly(phosphonate)s.

6. A method of treating nerve injury, spinal cord injury, myocardial infarction, stroke, bone injury, cartilage injury or wound healing said method comprising the hydrogel composition according to claim 1.

7. The method-according to claim 6, wherein said composition is administered to a site of treatment, a magnetic field is applied in order to anisotropically align the anisometric elements in a desired direction, and the matrix hydrogel composition is cross-linked in order to fix the orientation of the anisometric elements as aligned by said magnetic field in the range of 0.1 mT 1.5 T, preferentially 100-600 mT wherein the cross-linked matrix hydrogel has a Young's modulus in the range of 50 Pa 10 kPa.

8. The method according to claim 7, wherein the parallel distance between neighboring anisometric elements within the cross-linked matrix hydrogel is in the range of 0.1-100 μm, preferably 3-75 μm.

9. The method according to claim 7, wherein fibrinogen is used as matrix hydrogel composition and crosslinking is performed by adding thrombin in an amount sufficient to crosslink the matrix hydrogel composition.

10. The hydrogel composition according to claim 1, wherein the magnetic particles are superparamagnetic iron oxide particles.

11. The hydrogel composition according to claim 10, wherein the superparamagnetic iron oxide nanoparticles are present in the microgels in an amount of 0.0001 to 10 vol.-%.

12. The hydrogel composition according to claim 11, wherein the superparamagnetic iron oxide nanoparticles are present in the microgel elements in an amount of 0.001 to 2 vol.-%.

13. The hydrogel composition according to claim 1, wherein the microgel elements are present in the injectable hydrogel composition in an amount of 1 to 3 vol.-%.

* * * * *